US011395938B2

(12) United States Patent
Davis et al.

(10) Patent No.: US 11,395,938 B2
(45) Date of Patent: Jul. 26, 2022

(54) RESPIRATORY TRAINING SYSTEM

(71) Applicant: EVOLVED, LLC, Austin, TX (US)

(72) Inventors: Aaron Davis, Austin, TX (US); Patrick Estes, Austin, TX (US); Brian Kozak, Austin, TX (US)

(73) Assignee: EVOLVED, LLC, Austin, TX (US)

( * ) Notice: Subject to any disclaimer, the term of this patent is extended or adjusted under 35 U.S.C. 154(b) by 266 days.

(21) Appl. No.: 16/778,545

(22) Filed: Jan. 31, 2020

(65) Prior Publication Data
US 2020/0246659 A1    Aug. 6, 2020

Related U.S. Application Data

(60) Provisional application No. 62/799,542, filed on Jan. 31, 2019.

(51) Int. Cl.
*A63B 23/18*    (2006.01)
*A61M 16/00*   (2006.01)
(Continued)

(52) U.S. Cl.
CPC ....... *A63B 23/185* (2013.01); *A61M 16/0078* (2013.01); *A61M 16/20* (2013.01);
(Continued)

(58) Field of Classification Search
CPC .............. A63B 23/185; A63B 24/0062; A63B 71/0686; A63B 2071/0625; A63B 2071/0655; A63B 2230/40; A63B 71/0622; A63B 2071/0627; A63B 2071/065; A63B 2071/0675; A63B 2071/068; A63B 2208/0204; A63B 2208/0219; A63B 2208/0252; A63B 2208/0257; A63B 2209/08; A63B 2214/00; A63B 2220/17; A63B 2220/51; A63B 2220/56; A63B 2220/80; A63B 2220/805; A63B 2220/808; A63B 2220/833; A63B 2225/50;
(Continued)

(56) References Cited

U.S. PATENT DOCUMENTS 2,934,060 A * 4/1960 Satter .................... A61M 21/00
                                                                         600/27
4,487,207 A * 12/1984 Fitz ........................ A63B 23/18
                                                                         482/1
(Continued)

OTHER PUBLICATIONS

Powerlung, Inc., Respiratory Training System, accessed on Jan. 30, 2020, http://www.powerlung.com/region/us/.

*Primary Examiner* — Sundhara M Ganesan
(74) *Attorney, Agent, or Firm* — Dickinson Wright PLLC

(57) ABSTRACT

A system for respiratory training including a housing, a respiratory air channel disposed within the housing, a sensor configured to detect a breathing indicator and transmit a breathing indicator signal, a haptic device disposed within the housing, a processor operatively coupled to the sensor and the haptic device, and a memory device operatively coupled to the processor. The memory device includes instructions that, when executed by the processor, cause the processor to receive the breathing indicator signal from the sensor; generate a breath determination based on the breathing indicator signal; and responsive to the breath determination, cause the haptic device to generate a vibration.

17 Claims, 13 Drawing Sheets

(51) Int. Cl.
*A61M 16/20* (2006.01)
*A63B 24/00* (2006.01)
*A63B 71/06* (2006.01)

(52) U.S. Cl.
CPC ...... *A63B 24/0062* (2013.01); *A63B 71/0686* (2013.01); *A61M 2205/8206* (2013.01); *A63B 2071/0625* (2013.01); *A63B 2071/0655* (2013.01); *A63B 2230/40* (2013.01)

(58) Field of Classification Search
CPC ......... A63B 2230/207; A63B 2230/50; A61M 16/0078; A61M 16/20; A61M 2205/8206
See application file for complete search history.

(56) References Cited

U.S. PATENT DOCUMENTS

| | | | |
|---|---|---|---|
| 4,981,295 A * | 1/1991 | Belman | A61B 5/087 |
| | | | 482/13 |
| 5,395,301 A | 3/1995 | Russek | A61H 31/00 |
| | | | 601/41 |
| 6,212,135 B1 * | 4/2001 | Schreiber | A63B 23/185 |
| | | | 368/107 |
| 2004/0146842 A1 | 7/2004 | Carlucci et al. | |
| 2009/0239711 A1 * | 9/2009 | Foley | A63B 71/0619 |
| | | | 482/13 |
| 2009/0264255 A1 * | 10/2009 | Tutsch | A63B 23/18 |
| | | | 482/13 |
| 2010/0160118 A1 * | 6/2010 | Shirasaki | A61B 5/0816 |
| | | | 482/13 |
| 2011/0124470 A1 * | 5/2011 | Spurling | A63B 23/18 |
| | | | 482/13 |
| 2011/0313239 A1 * | 12/2011 | Ahne | A63B 23/185 |
| | | | 600/27 |
| 2013/0190554 A1 * | 7/2013 | Vogt | A63B 23/185 |
| | | | 600/27 |
| 2014/0046121 A1 * | 2/2014 | Gillies | A61B 5/743 |
| | | | 600/27 |
| 2014/0106324 A1 * | 4/2014 | Adams | A61B 5/6898 |
| | | | 434/262 |
| 2015/0011906 A1 * | 1/2015 | Wallach | A61B 5/7455 |
| | | | 600/538 |
| 2016/0049096 A1 * | 2/2016 | Bruin | A63B 23/185 |
| | | | 434/262 |
| 2016/0193436 A1 * | 7/2016 | Khasawneh | A61M 16/0006 |
| | | | 128/202.16 |
| 2016/0317865 A1 * | 11/2016 | Acosta | G09B 15/00 |
| 2016/0346603 A1 * | 12/2016 | Halliday | A61M 16/208 |
| 2018/0318642 A1 * | 11/2018 | Lunz | A61M 16/0066 |
| 2018/0318643 A1 * | 11/2018 | Klee | A61M 16/026 |
| 2018/0339122 A1 * | 11/2018 | Lunz | A63B 21/00069 |
| 2019/0134460 A1 * | 5/2019 | Cheu | A61M 16/024 |
| 2019/0201743 A1 * | 7/2019 | Meyer | A61M 16/208 |
| 2019/0290959 A1 * | 9/2019 | Chesbrough | A61B 5/087 |
| 2019/0299055 A1 * | 10/2019 | Poulsen | A61B 5/224 |
| 2020/0038708 A1 * | 2/2020 | Cheu | A61B 5/6823 |
| 2020/0297960 A1 * | 9/2020 | O'Donnell | A61M 16/0063 |
| 2020/0329979 A1 * | 10/2020 | Shantharam | A61B 5/0816 |

* cited by examiner

Prior Art

*Prior Art*

RESPIRATORY TRAINING SYSTEM

CROSS-REFERENCE TO RELATED APPLICATION

This application claims priority to and the benefit of U.S. Provisional Application Ser. No. 62/799,542, filed Jan. 31, 2019, the entire disclosure of which is hereby incorporated by reference.

BACKGROUND

The present disclosure relates generally to systems for respiratory training. Respiratory training may allow users, such as athletes and patients, to improve their cardiovascular functionality.

SUMMARY

This section provides a general summary of the present disclosure and is not a comprehensive disclosure of its full scope or all of its features, aspects, and objectives.

Disclosed herein are implementations of a system for respiratory training in accordance with aspects of the present disclosure. The system includes a housing, a respiratory air channel disposed within the housing, a sensor configured to detect a breathing indicator and transmit a breathing indicator signal, a haptic device disposed within the housing, a processor operatively coupled to the sensor and the haptic device, and a memory device operatively coupled to the processor. The memory device includes instructions that, when executed by the processor, cause the processor to receive the breathing indicator signal from the sensor; generate a breath determination based on the breathing indicator signal; and responsive to the breath determination, cause the haptic device to generate a vibration.

Also disclosed herein are implementations of a system for respiratory training in accordance with aspects of the present disclosure. The system includes a housing, a respiratory air channel disposed within the housing, a sensor configured to detect a breathing indicator and transmit a breathing indicator signal, and a haptic device disposed within the housing and, configured to provide haptic feedback in response to the breathing indicator signal.

Also disclosed herein is a system for providing a user with breath training feedback in accordance with aspects of the present disclosure. The system includes a display, a network device, a processor operatively coupled to the display and the network device, and a memory device operatively coupled to the processor. The memory device includes instructions that, when executed by the processor, cause the processor to: determine a target breathing rate, receive breathing information about a user's breathing from a respiratory training device, and generate a breath determination of whether the user's breathing rate is above or below the target breathing rate.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, independent of whether those elements are in physical contact with one another. The terms "transmit," "receive," and "communicate," as well as derivatives thereof, encompass both direct and indirect communication. The terms "transmit," "receive," and "communicate," as well as derivatives thereof, encompass both communication with remote systems and communication within a system, including reading and writing to different portions of a memory device. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable storage medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable storage medium" includes any type of medium capable of being accessed by a computer, such as read only memory (ROM), random access memory (RAM), a hard disk drive, a compact disc (CD), a digital video disc (DVD), solid state drive (SSD), or any other type of memory. A "non-transitory" computer readable storage medium excludes wired, wireless, optical, or other communication links that transport transitory electrical or other signals. A non-transitory computer-readable storage medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

The drawings as discussed may include additional and/or fewer components and/or steps in an alternative order and are not limited to those illustrated in this disclosure.

DETAILED DESCRIPTION

Figures 1, 1A, 1B:
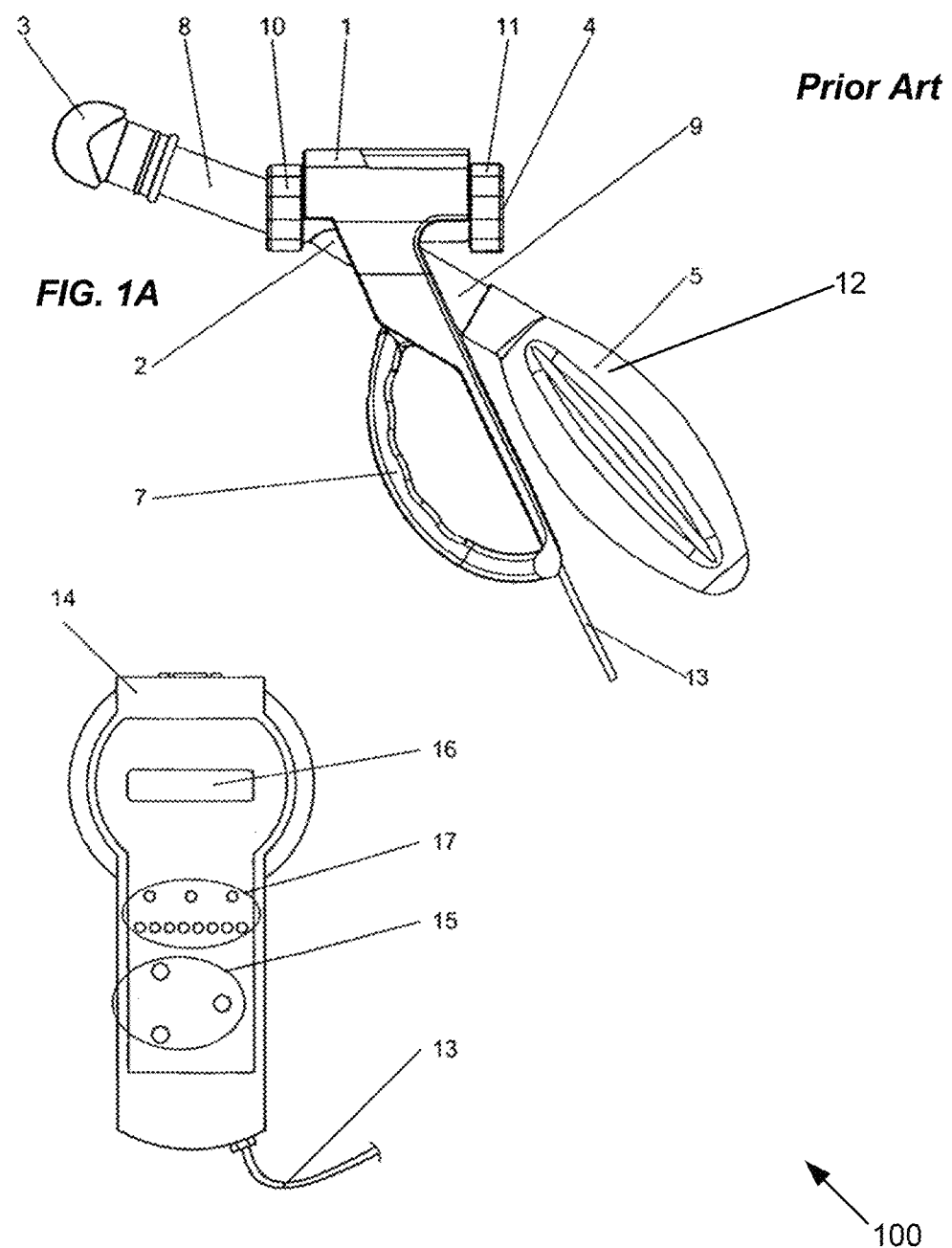
FIG. 1 is an overall view of a prior art respiratory training device, which includes a main device in FIG. 1A and control device in FIG. 1B in accordance with aspects of the present description.

FIG. 1 illustrates a prior art respiratory training device. The prior art respiratory training device 100 illustrated in FIG. 1A includes a housing 1, a respiratory air channel 2 set into this housing 1, a mouthpiece 3, which is connected via a connection tube 8 with the respiratory air channel 2 and an air bag 5. The respiratory training device 100 is connected with a control device 14 via a cable or a data line 13. In the depicted example in FIG. 1B, the control device 14 includes a processor and memory storage device, which can also be part of a portable or stationary computer connected with the control device 14. The housing 1 has a handle 7 by which the respiratory training device 100 can be held manually. When the respiratory training device 100 is utilized, the user, such as a training person or a person to be treated therapeutically, inserts the mouthpiece 3 into his or her mouth for training or therapeutic purposes. After the respiratory passage through the nose is closed, for instance through the use of a nose plug or a nose clip, the user's breathing takes place entirely via the respiratory training device 100. The respiratory air of the user flows via the connecting tube 8 into the respiratory air channel 2. This respiratory air channel 2 has the form of a Y and branches into two channels, with one branch tube 9 leading to the air bag 5, and the respiratory air channel 2 leading to an inlet and outlet opening 4 for respiratory or fresh air. A valve configuration 6 is disposed in the respiratory air channel 2, which is described in further detail in FIGS. 2 to 4. The air bag 5 is detachable via a connection element 12 and connected with the branch tube 9 and air bags 5 with different volumes are available which are used depending on the pulmonary vital capacity of the training person.

During a breathing cycle, which starts, for example, with an exhalation process, the valve configuration 6 first closes the inlet and outlet opening 4 such that initially the flexible air bag 5 is filled with exhaled air. As soon as the air bag 5 is full, an overpressure develops in the respiratory air channel 2 and the valve configuration 6 opens the throughflow of respiratory air to the inlet/outlet opening 4. The remaining portion of exhaled air now flows via this outlet opening 4 into the ambient air. During the adjoining inhalation process, the valve configuration 6 is first closed again and therefore first the respiratory air contained in the air bag 5 is again inhaled. As soon as the air bag 5 is empty again, an underpressure is generated in the connecting tube 8 and in a portion of the respiratory air channel 2, which opens the valve configuration 6. For the remaining inhalation cycle, fresh air is inhaled via the inlet opening 4. Subsequently these processes repeat cyclically for each breathing cycle. To be able to carry out the desired training or therapeutic processes correctly, the respiratory frequency per minute is preset via the control device 14 and its input unit 15.

As illustrated in FIG. 1B, the breathing processes to be carried out by the training person are indicated in the depicted example on an indicator element 17 and on a second indicator element 16. The indicator elements 16, 17 may be on a display or provided through audio outputs. For example, the indicator elements 16, 17 may include corrections or error statements. In the case of the breathing process by the training person diverging from the preset data beyond a permissible discrepancy, the control device 14 or its display elements 16, 17 may indicate alarm signals. To ensure the correct operation of the respiratory training device 100, first the vital capacity of the lung of the user may be determined. The volume of the air bag 5 to be used and the breathing frequency at which the user is to breathe may be calculated or determined with the aid of tables. The particular training status and the desired course of training may be taken into consideration. For normal training processes, bags 5 with volumes from 0.5 L to 6 L in 0.5 L steps may be made available. For example, for a well-trained male, the vital capacity may be determined to be 5 L, and therefrom the volume of the air bag 5 at 50% of the vital capacity is obtained as 2.5 L. The respiratory minute volume depends on height and weight of the user and is, for example 150 L. The calculated respiratory frequency in this case is between 20 and 24 cycles/min.

Figure 2:
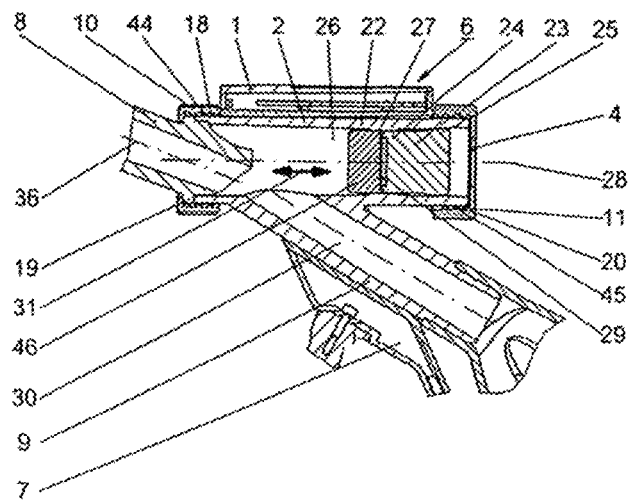
FIG. 2 is a longitudinal sectional view of a respiratory air channel in the piston valve the prior art respiratory training device of FIG. 1 in accordance with aspects of the present disclosure.

FIG. 2 illustrates a longitudinal section through the upper region of the housing 1 and the respiratory air channel 2 set therein with the valve configuration 6. The valve configuration is a piston valve 6. The respiratory air channel 2 is detachably set into the housing 1 and is detachably fastened by the connecting element 10 and the closure element 11. The connecting element 10 is disposed on the side of the housing 1 that the connecting tube 8 for mouthpiece 3 is disposed on. Outer threads 18 are disposed on the respiratory air channel 2, and the connecting element 10 has inner threads 44. The connecting tube 8 is connected by means of the connecting element 10 with the respiratory air channel 2 via a sealing ring 19 to form a retaining shoulder.

The respiratory air channel 2 is developed in the form of a Y and includes an air passage volume 26 and a flow channel 30 branching off therefrom. As described, the flow channel 30 leads to the air bag 5, which is connected across the connecting element 12 with the branch tube 9 of respiratory air channel 2. The piston valve 6 is disposed following the branching-off of the flow channel 30 in the portion of the respiratory air channel 2 facing away from the connecting tube 8. This piston valve 6 includes a housing part 22, which forms an integral component of the respiratory air channel 2. On the shell of the air passage volume 26 in the proximity of the housing part 22 a sealing face 27 is disposed and extends over only a sub-region in the direction of the flow axis 28. For example, in the depicted example, the sealing face 27 extends over 9 mm, and the diameter of the air passage volume 26 in the region of the sealing position is approximately 23 mm. The air passage volume 26 has a greater cross sectional area. In front of and behind the sealing face 27 than at the sealing face 27. A valve body 23 is set into the air passage volume 26 in the proximity of housing part 22. The valve body 23 includes a piston 24, a guide part 25, and guide part 46. The valve body 23 is slidingly guided via the piston 24 and the guide part 25 in the air passage volume 26 of the respiratory air channel 2 and freely movable in the directions of arrows 31. The movement of the valve body in the direction of arrows 31 or in the direction of the flow axis 28 in the air passage volume 26 is delimited by end stops 42, 43 shown in FIG. 4. The installation and removal of the valve body 23 takes place from that side of the respiratory air channel 2 on which the inlet/outlet opening 4 is disposed. Outer threads 20 are disposed at the end region of the respiratory air channel 2 to engage with with inner threads 45 on closure element 11. FIG. 2 illustrates the flow axis 28 of the air passage volume 26 in the region of the piston valve 6 coinciding with the longitudinal axis 36 of respiratory air channel 2. By removing the connecting element 10 and the closure element 11, as well as connecting element 12, the various structural components of the respiratory training device 100 can be separated from one another in a simple manner. The respiratory air channel 2 may be formed simply, such that the elements can be easily cleaned. The valve body 23 may be formed to be easy to clean. This also applies to the other structural components which come into contact with respiratory air, such as the mouthpiece 3, the connecting tube 8 and the closure element 11. All of these structural components can be produced of a material which, if necessary, is sterilizable. The installation and removal of the valve body 23 can take place in a simple manner, because it does not have a direct mechanical connection to the housing part 22 or respiratory air channel 2. This leads to considerable simplification of the cleaning and handling of the device. For example, any person utilizing the respiratory training device 100 can associate parts contaminated with respiratory air with a specific person.

The housing 1 and the control device 14 can be utilized by different users because the housing 1 and the control device 14 do not come into contact with respiratory air. In normal cases, superficial cleaning of the housing and the control device 14 is sufficient. All parts of the respiratory training device 100 that come into contact with respiratory air from a user can be exchanged in simple manner, such that the respiratory training device 100 is immediately available for another user to utilize.

Figure 3:
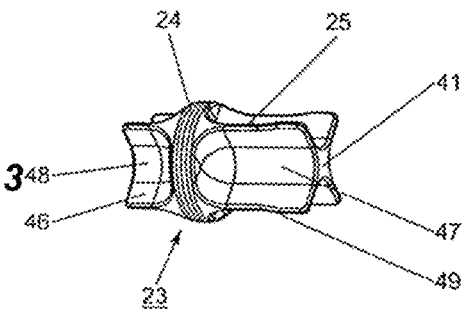
FIG. 3 is a perspective view of the valve body of the piston valve of the prior art respiratory training device in accordance with aspects of the present description.

FIG. 3 illustrates a valve body 23 according to the aspects of the description, which is a component of the piston valve 6. Adjoining piston 24 is, on the one side, the guide part 25 and, on the opposing side, the guide part 46. The two guide parts 25 and 46 include four symmetrically disposed ribs. Flow channels 47, 48 for air are located between the ribs. The guide part 25 has a greater diameter than the piston 24 in the end region 41 of guide part 25, facing away from piston 24. Stop faces 49 are disposed between piston 24 and end region 41, where the diameter of the ribs of guide part 25 is reduced. The diameter of the ribs of the guide part 46 is also reduced relative to piston 24.

Figure 4:
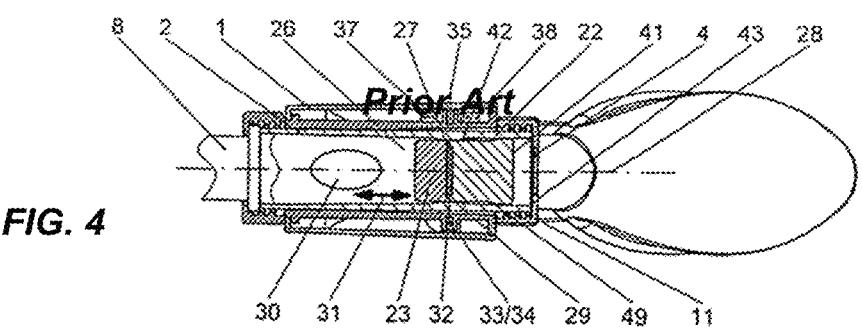
FIG. 4 is a cross-sectional view of the respiratory air channel of the prior art respiratory training device in accordance with aspects of the present disclosure.

FIG. 4 illustrates a cross section through respiratory air channel 2 along axis 36 according to FIG. 2. In this illustration, the force-generating means 29 retains the valve body 23 in the sealing position or determines the opening forces for the piston valve 6 and is disposed in the proximity of the housing part 22. In the depicted example, the force-generating means 29 includes magnetic elements, and the valve body 23 includes a structural component 32 of a magnetic material. Two structural components 34 made of magnetic material are disposed in the proximity of the housing part 22 of valve 6 means. These structural components 32, 34 are positioned in the sealing position of valve body 23 in a common radial plane 35 with respect to the flow axis 28 of the air passage volume 26. The two structural components 34 are permanent magnets, i.e. magnetic elements of a magnetically hard material. The magnetic structural component 32 in valve body 23 is also formed by a permanent magnet or includes a magnetically hard material. The axes of the magnetic elements 32 and 34 extend approximately parallel to the flow axis 28 and the pole configurations are oriented identically aligned. The two magnetic structural components 34 are disposed in the housing 1 symmetrically to the flow axis 28 and abut the housing part 22 of piston valve 6. Through the magnetic field generated by the two magnetic elements 34 the magnetic structural component 32 is positioned in the piston 24 or valve body 23 approximately in plane 35 and therewith the valve body 23 is held in the sealing position. The effective magnetic forces are determined in known manner such that the valve body 23 is only displaced at a desired under- or over-pressure one of the directions of arrows 31 from the sealing position. It is also possible to employ in the housing 1 or in the proximity of the housing part 22 of piston valve 6, instead of permanent magnets 34, electromagnets 33, which are activated by electric current. The appropriate current supply and control signal supply is carried out from the control device 14 via the cable 13 and further, not shown, connection lines in housing 1. This configuration permits changing the opening forces for opening the piston valve 6 as can be useful in training the user's breathing force (e.g. by increasing the force that the user needs to apply to open the valve). Furthermore, the valve opening times can also be affected and controlled from the control device. A further embodiment includes that in the valve body 23 the magnetic element is formed of a permanent magnet 32 and in the housing part 1 the magnetic elements are formed of a magnetically soft material, for example iron, and usefully an annular element can be utilized. The same configuration is also possible conversely in that the magnetic structural component 32 in the valve body 23 includes a magnetically soft material, for example iron, and the two magnetic structural components 34 in the proximity of the valve housing 22 include a magnetically hard material, i.e. of a permanent magnet. Two sensors 37, 38 are disposed spaced apart from the sealing plane 35 and on both sides of the sealing position, between piston 24 and sealing face 27 on housing part 22. The sensors 37, 38 may be Hall sensors, which, can detect changes of the magnetic field caused by the displacement of the valve bodies 23 or its magnetic structural component 32. The same functions can also be acquired by reed sensors, optical sensors or pressure sensors. By means of these sensors 37 or 38 it is possible to detect whether or not the valve body 23 is located in the opening position for the inhalation of fresh air or in the opening position for the ejection of respiratory air through opening 4. The opening position for the inlet of fresh air through opening 4 is determined by a stop 42 at the end of sealing face 27 and a stop 49 on the ribs of guide part 25. The sensor 37 detects this opening position (or first position) and the length of time of the opening. The opening position of the valve body 23 for the outlet of consumed air through opening 4 is determined by the end region 41 on guide part 25 and the inner face on closure element 11, which forms an end stop 43. The sensor 38 is assigned to this opening position (second position) and detects the opening status and the length of time of the opening. The sensors 37, 38 may each be configured to transmit one or more breathing indicator signals, indicating the position of the valve body 23. In these movements in one of the directions of the arrows 31 from the sealing position into the particular opening position, the valve body 23 slides in the air passage volume 26, with this sliding movement generating only very low friction losses. In this configuration, necessary forces for excursion from the sealing position into the opening position do not progressively increase the further the excursion of the body, but such force rather either stays constant or decreases. The valve body 23, upon exceeding the holding force in the sealing position, is immediately completely displaced into the opening position and therewith the entire throughflow cross section for the air is released. Therewith the throughflow quantity of air is sufficiently determined with sufficient precision by the opening times of the piston valve 6.

Figure 5:
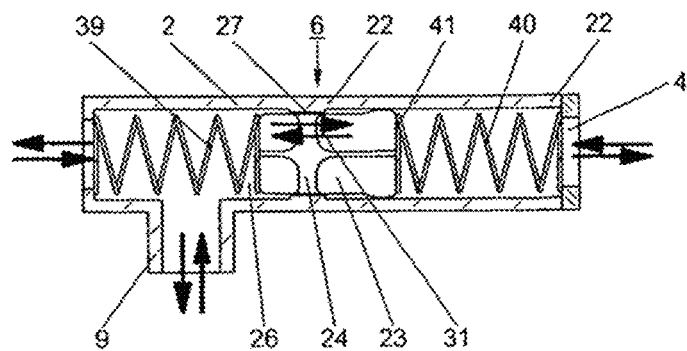
FIG. 5 is a cross-sectional view of a valve configuration of the prior art respiratory training device shown schematically with springs as force-generating means in accordance with aspects of the present description.

FIG. 5 illustrates the respiratory air channel 2 and the piston valve 6 in schematic representation. The housing 1 and the remaining attachment parts are not shown. The housing part 22 of piston valve 6 is an integral component of the respiratory air channel 2. The housing part 22 includes the sealing face 27 and on valve body 23 the piston 24 is correspondingly disposed. The formation of valve body 23 and sealing face 27 corresponds to the embodiments according to FIGS. 2 and 3. The force-generating means 29 in this embodiment example are, however, not formed by magnetic elements but rather by the two flat coil springs 39 and 40. The forces of these two flat coil springs 39 and 40 retain the valve body 23 in the sealing position and permit a displacement in the directions of the two arrows 31. Therewith the same operational function as described in FIGS. 1 to 4 results. This embodiment can be applied in specific cases, where a device as cost-effective as possible is desired and also a progressive increase of the opening forces on the valve body 23 can be tolerated, i.e., a device for which a lower operating precision is permitted.

Figure 6:
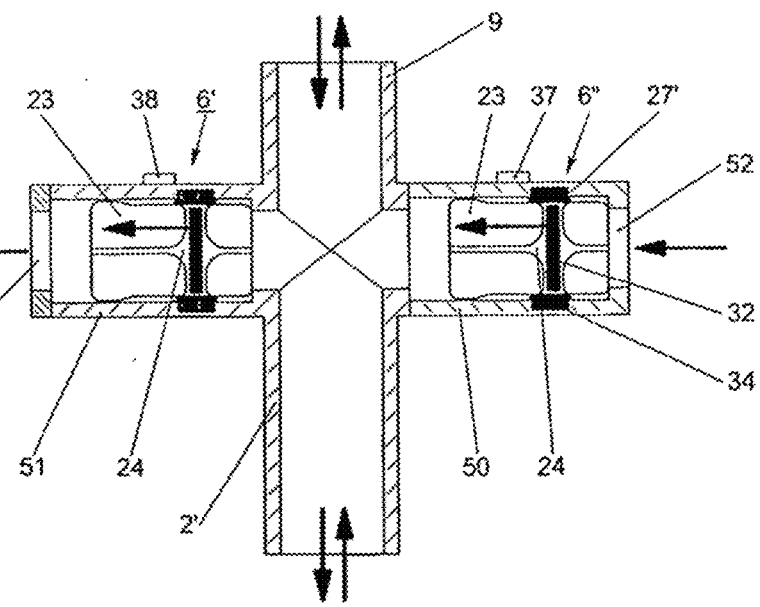
FIG. 6 is a cross-sectional view of a the respiratory air channel of the prior art respiratory training device with two piston valves in accordance with aspects of the present description.

The respiratory training device 100 according to the aspects of the description can also be equipped with two piston valves 6' and 6" as shown schematically in FIG. 6. A respiratory air channel 2' includes two laterally branching tube pieces 50, 51, which each have either an inlet opening 52 or an outlet opening 53 disposed at each of their respective outer ends. The respiratory air channel 2 also has a branch-off tube 9 leading to the air bag 5. In each of the two tube pieces 50, 51, a valve body 23 is disposed whose embodiment corresponds to the valve body according to FIG. 3. The two valve bodies 23 each include a piston 24, in which a magnetic structural component in the form of a permanent magnet 32 is installed. The sealing face 27', which cooperates with piston 24, is disposed on the inner shell of tube pieces 50, 51. Two diametrically opposing magnetic structural components in the form of permanent magnets 34 are installed in the proximity of the sealing face 27' in the tube pieces 50 and 51. The two valve bodies 23 in this formation can be displaced only from the sealing position in one direction into an opening position.

The valve 6" in tube piece 50 has the function of drawing in fresh air via the opening 52. The opening position of the valve body 23 is detected via the sensor 37 and also the opening time is determined. Valve 6' in tube piece 51, in comparison, has only the function of making possible the outlet of consumed air through opening 53 and specifically if the air bag 5 is filled. Here also the opening position and the opening time of the valve body 23 is determined via the sensor 38. This configuration with two piston valves 6' and 6" makes it possible to fix different opening points in time for the drawing-in of fresh air or the opening time point for the outlet of respiratory air into the environment. This can be useful and of interest for certain training and/or therapy programs.

In a method according to the aspects of the description for monitoring the fresh air supply on the respiratory training device 100 basic data are partially used, which were determined in experimental series on test subjects. Especially the vital capacity depends on the person and the respiratory limit value depends on the person and on the sex. For the determination by calculation of the respiratory frequency of a specific person the following approach may be used. First, in known manner, the vital capacity (Vc) is measured. The volume of the air bag 5 is fixed such that it is 50% of the vital capacity. Additionally, the respiratory limit value (MVV) is determined and specifically according to the following function:

Men: $MVV=(1.193\times height)-(0.816\times age)-37.949$

Women: $MVV=(0.0842\times height)-(0.685\times age)-4.868$

Height must be stated in cm and age in years.

For endurance training a respiratory minute volume (AMV) is recommended, which is 60% of the respiratory limit value (MVV).

Determining the respiratory frequency (1/min) is carried out according to the function respiratory frequency+AMV/1.5×bag volume.

If training takes place in the range of these values, it is ensured that the training person does not have too much $CO_2$ (hypercapnic) or too little $CO_2$ (hypocapnic) in the respiratory air. Depending on the fixing of the limit values for the $CO_2$ content in the respiratory air, constants adapted in the formulas are inserted. These functions and table values apply to healthy average persons. For untrained persons, other person groups or, for example, ill persons, individual clarifications and adaptations may be used.

In some embodiments of the present disclosure, the magnetic structural components 34 disposed in the housing 1 are set into the housing 1 and configured so as to not dislodge during training or after multiple uses.

In some embodiments, the breathing indicator signals include $CO_2$ concentration, $O_2$ concentration, or any other desired breathing indicator signal.

FIGS. 7-10 illustrate an example of a respiratory training device 700 in accordance with aspects of this disclosure.

The respiratory training device 700 may include any suitable combination of the elements of the prior art respiratory training device 100 shown in FIGS. 1-6 and described above. The respiratory training device 700 may further include more or fewer components than those discussed in this disclosure.

Figure 7:
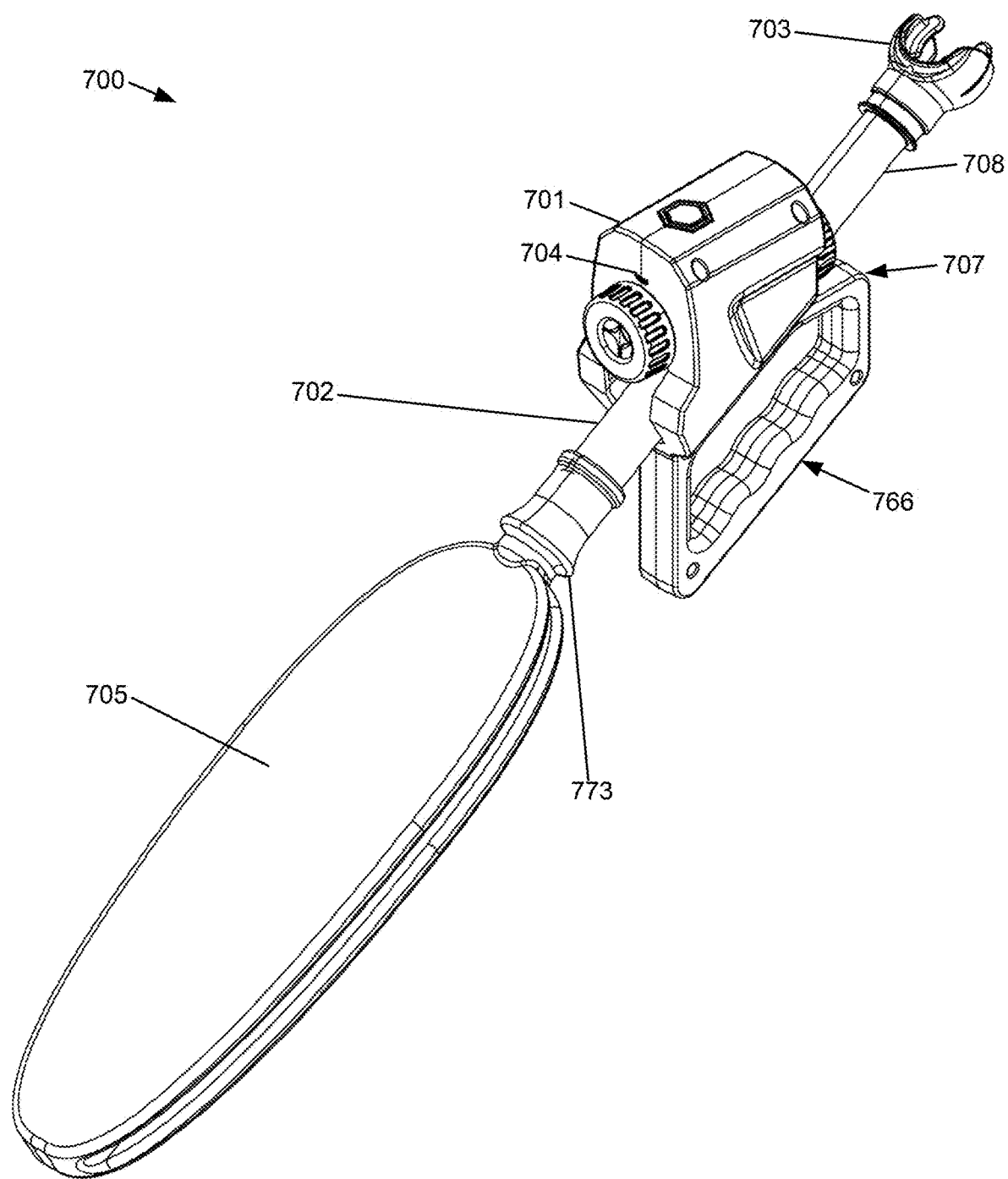
FIG. 7 is a perspective view of a respiratory training device in accordance with aspects of the present disclosure.
Figure 8:
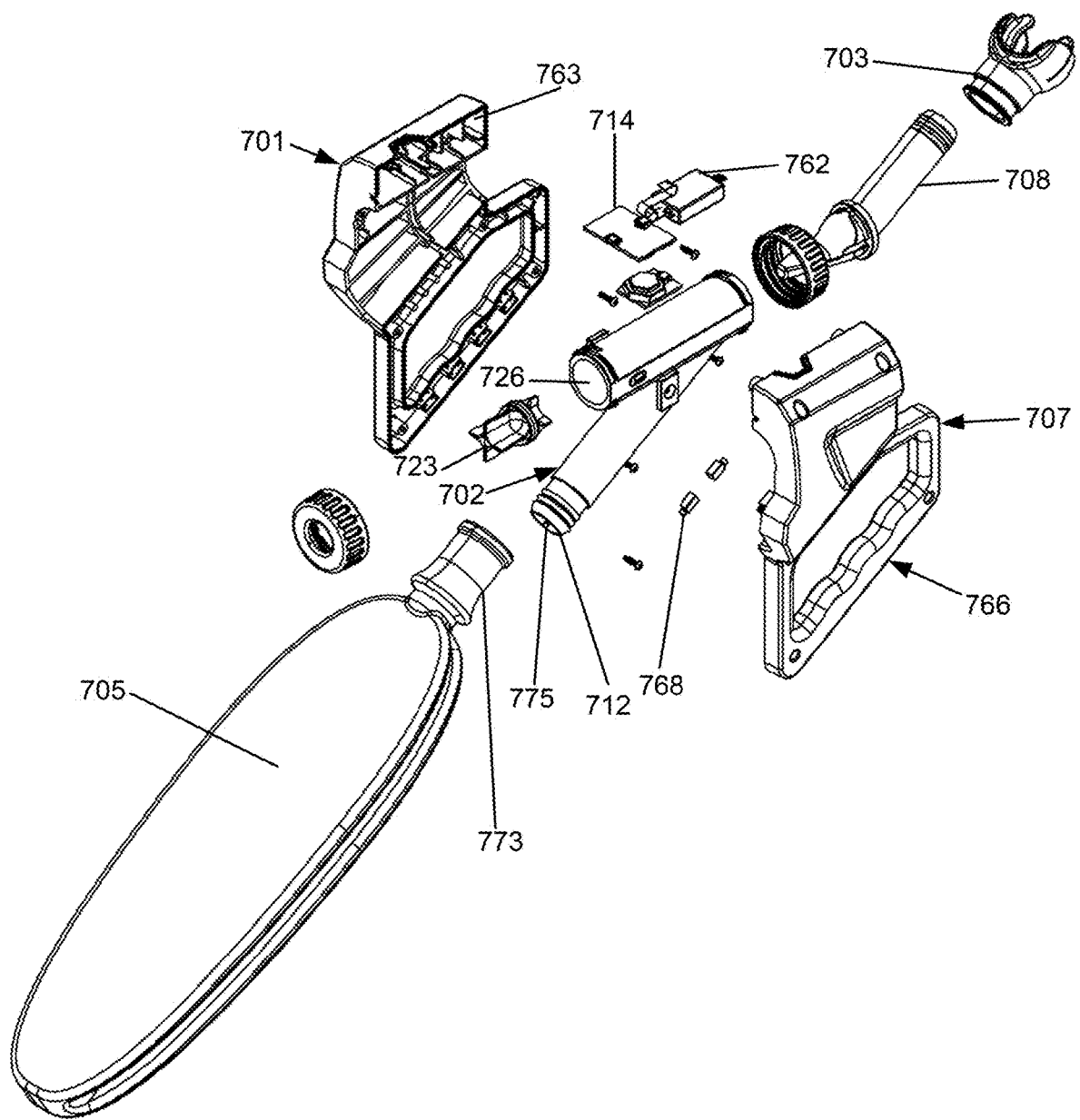
FIG. 8 is an exploded perspective view of the respiratory training device of FIG. 7 in accordance with aspects of the present disclosure.
Figure 9:
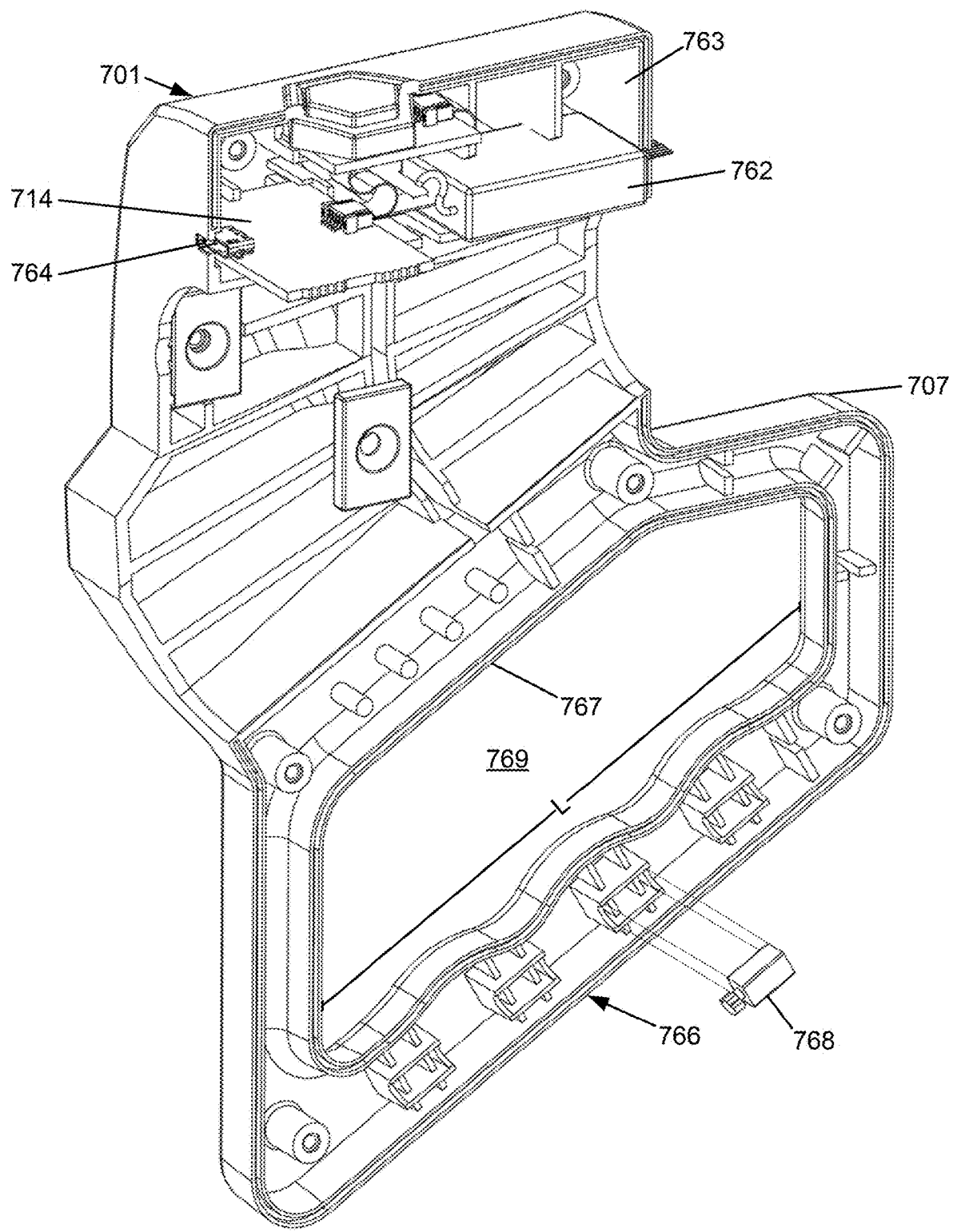
FIG. 9 is a perspective cross-sectional view of a portion of the respiratory training device of FIG. 7 in accordance with aspects of the present disclosure.
Figure 10:
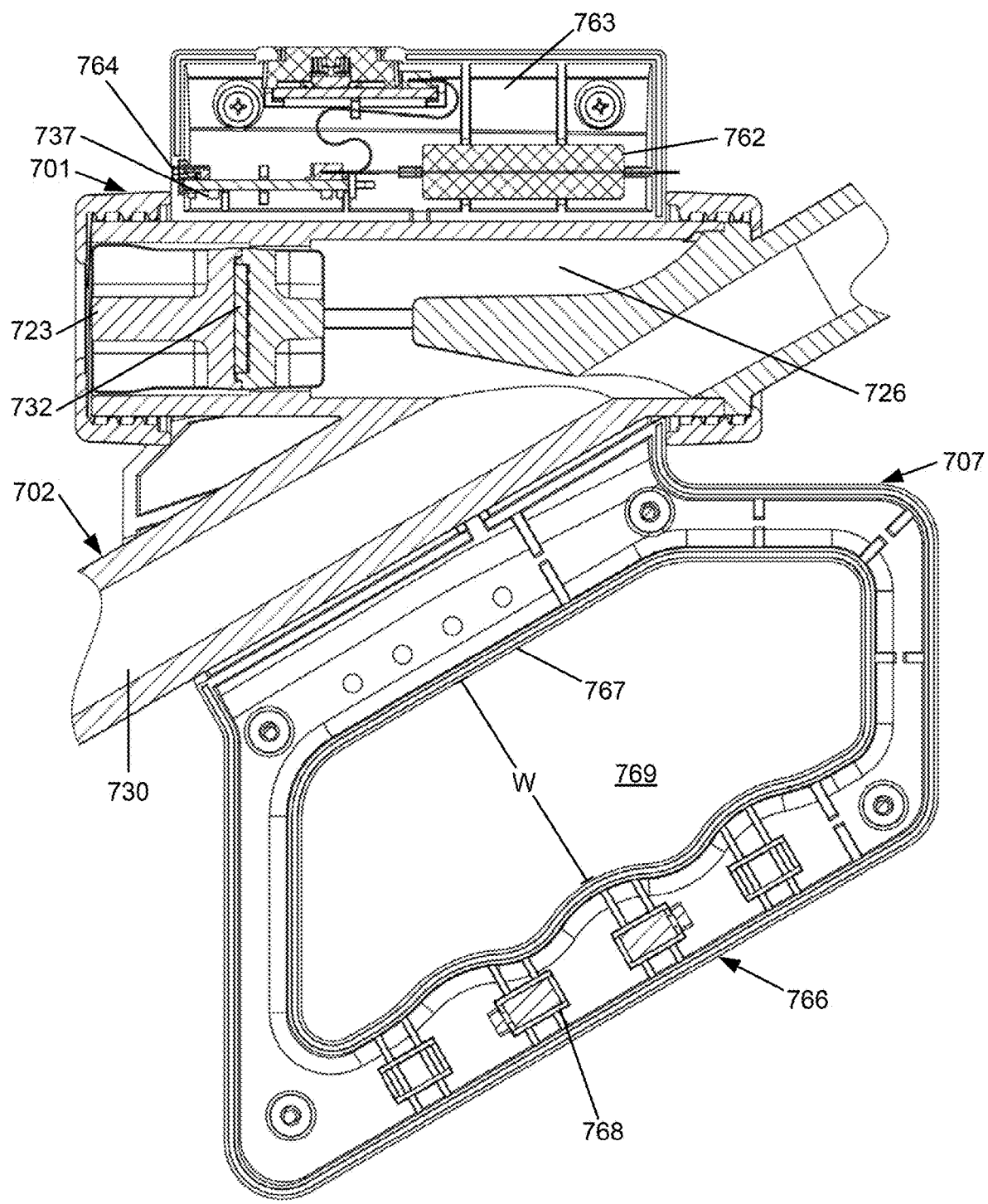
FIG. 10 is a cross-sectional view of a portion of the respiratory training device of FIG. 7 in accordance with aspects of the present disclosure.

As best illustrated in FIGS. 7 and 8, the respiratory training device 700 may include a housing 701, a respiratory air channel 702 set into the housing 701, and a mouthpiece 703 connected to the respiratory air channel 702 by a connection tube 708. The housing 701 may be made out of a Nylon compound, any other suitable material, or any combination thereof. The housing 701 may be made using selective laser sintering (SLS) processing or using any other suitable process. The respiratory air channel 702 may form a Y shape and includes an air passage volume 726 and a flow channel 730 branching off therefrom. A valve body 723 including a magnetic structural component 732 may be set into the air passage volume 726. A sensor 737 may be disposed in the air passage volume 726. The sensor 737 may be a Hall sensor, which may detect changes of the magnetic field generated with by displacement of the valve body 723 or the magnetic structural component 732 of the valve body. There may be more than one sensor 737. The sensor 737 may also be a reed sensor, optical sensor, pressure sensor, any other suitable sensor type, or any combination of the above.

The respiratory training device 700 may include a connection element 712 for coupling to an air bag 705. The air bag 705 may include an air bag coupling element 773. The air bag coupling element 773 may be integral to the air bag 705. The air bag coupling element 773 may be removable from the air bag 705 for attaching to other air bags. The connection element 712 may be a male-female connector or any other suitable connector. The connection element 712 may include a sensor 775 for detecting a feature of the air bag 705. For example, the air bag 705 may include its size information (e.g. 2.5 L, 3 L, etc.) and an indicator (e.g., a bar code) that contains the size information, such that the sensor (e.g., a bar code reader) can read the indicator to obtain the size information. The size information may be used for calculating breathing volume or transmitting to a remote device for display.

The respiratory training device 700 may include a control device 714. The control device 714 may include a processor 1102 and a memory device 1104. The control device 714 may include an input, such as a touchscreen, a mouse, a keyboard, a microphone, or any other suitable input. The control device 714 may include network device 1110. The network device 1110 may be wired or wireless. The control device 714 may include a battery 762. The battery 762 may be a rechargeable lithium battery or any other suitable battery. The battery 762 may have a battery life of 6-8 hours or any other suitable battery life. The housing may include a compartment 763. The control device 714 and the battery 762 may be disposed in the compartment 763. The control device 714 and the battery 762 may be placed such that the battery 762 is above the respiratory air channel 702 when the respiratory training device 700 is being used. The compartment may be disposed opposite the handle 707. Placing the control device 714 and the battery 762 above the respiratory air channel 702 may prevent corrosion resulting from condensed moisture from the user's breath. The control device 714 may include a port 764 for receiving a wired connection. The port may be a USB-C port. The wired connection may be configured to provide data transfer to and from the control device. The wired connection may be configured to charge the battery 762. The control device 714 may be in communication with the sensor 775 of the connection element 712 for receiving data about the detected feature of the air bag 705.

The housing 701 may include a handle 707 having a grip portion 766 configured to provide a grip for the user to hold onto the respiratory training device 700. The grip portion 766 may include a grooved surface 771 for receiving the user's hands or fingers. The handle may be disposed opposite the compartment 763. The grip portion 766 may have a length L that is at least 5 inches in length to accommodate one or two hands being disposed on or adjacent each other about the handle. The length L may be at least 6 inches in length to accommodate one or two hands being disposed on or adjacent each other about the handle. The length L may be at least 7 inches in length to accommodate one or two hands being disposed on or adjacent each other about the handle. The handle 707 may define a handle opening 769, having a width W between the grooved surface 771 of the grip portion 766 and an opposite portion 767 of the handle 707 opposite the grip portion 766. The width W may include dimensions to accommodate one or more hands, such as overlapping hands, to hold onto the handle 707 wherein the fingers of the user's hand(s) are positioned through the opening # and bend around the grip portion 766 of the handle 707. For example, the width W may be at least 1 inch to allow for one or more hand to grip the grip portion 766. The width W may be at least 1.25 inches. The width W may be at least 1.5 inches. The width W may be at least 1.75 inches. The width W may be at least 2 inches. The width W may be at least 2.25 inches. The width W may be at least 2.5 inches. The width W may be at least 2.75 inches. The width W may be at least 3 inches. The width W may be between 1 inch and 2 inches. The width W may be between 1.25 inches and 1.75 inches. The width W may be between 1.5 inches and 1.75 inches. The width W may be any suitable dimension or range of dimensions. The handle 707 can be configured to include variable dimensions, such that the width W can be adjusted to accommodate different sized hands (e.g., woman's hands, man's hands).

The handle 707 may include a haptic device 768. The haptic device 768 may be disposed within the grip portion 766 of the handle 707. The haptic device 768 may be in communication with the control device 714. The haptic device 768 may be configured to provide haptic feedback to the user. The haptic device 768 may be configured to provide the haptic feedback based on a breath determination by the processor 1102 of the control device 714 that the user is overbreathing or underbreathing. The haptic device 768 may be configured to provide one or more vibration patterns, such a multiple vibration patterns being generated in a sequence and/or simultaneously. The haptic device 768 may be configured to provide different vibration patterns based on different breath determinations of the processor 1102. Examples of different vibration patterns include one short vibration, one long vibration, multiple short vibrations, multiple long vibrations, differently spaced vibrations, any other suitable vibration pattern, and any combination thereof. The haptic device 768 may be an eccentric rotating mass actuator, linear resonant actuator, piezoelectric actuator, any other suitable haptic device, or any combination thereof.

Figure 11:
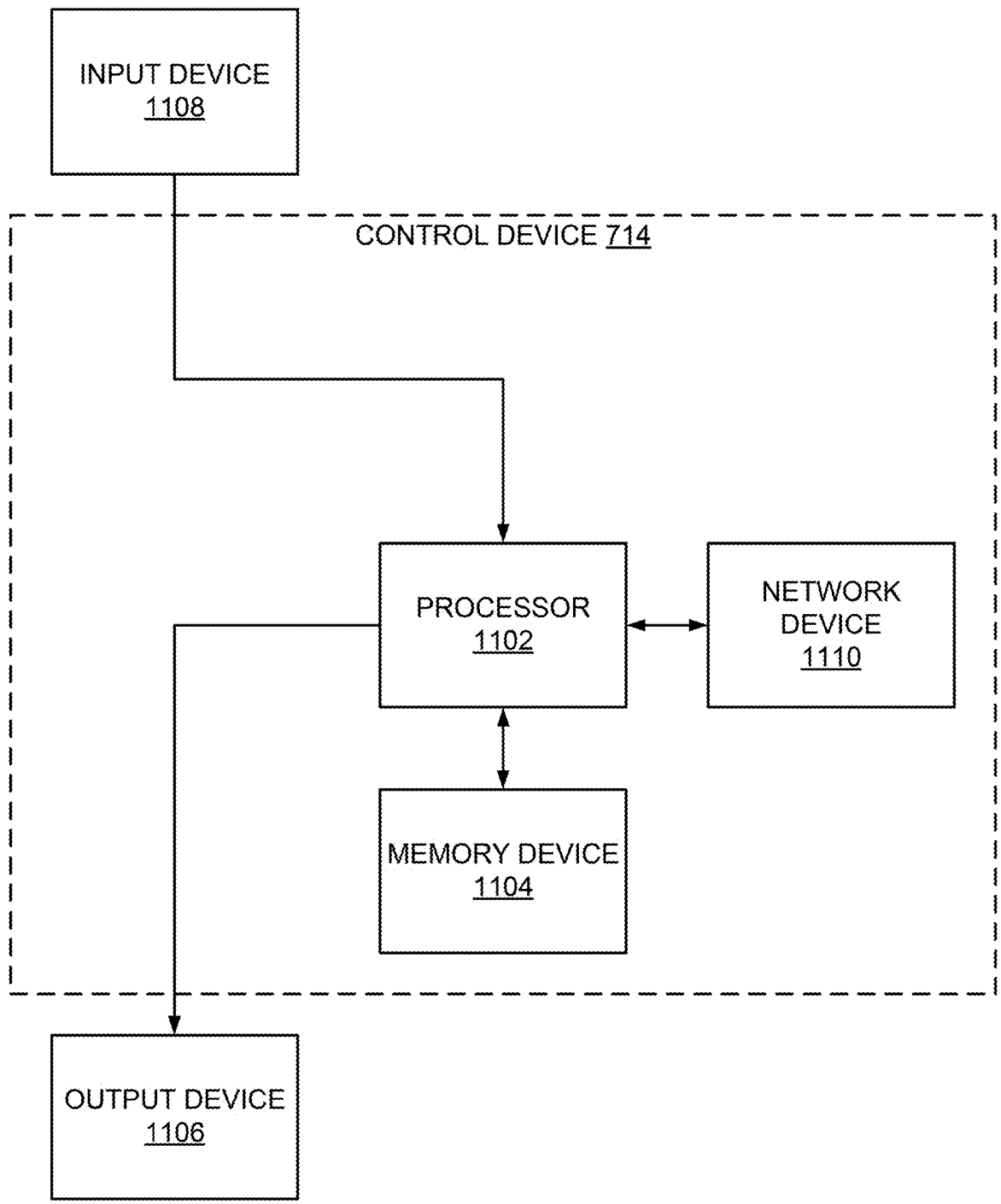
FIG. 11 is a block diagram of a control device of a respiratory training device of FIG. 7 in accordance with aspects of the present disclosure.

FIG. 11 generally illustrates a block diagram of the control device 714 of the respiratory training device 700. The control device 714 may include the processor 1102 according to principles of the disclosure. The processor 1102 may be disposed within the housing 701 adjacent the battery 762 or at any other suitable location within the respiratory training device 700. The control device 714 may include a memory device 1104 in communication with the processor 1102. The memory device 1104 may be a hard-disc memory device, a solid state memory device, ROM, RAM, any other suitable memory device, or any combination thereof. The memory device 1104 may include instructions that cause the processor 1102 to perform certain operations, such as the methods disclosed herein.

In some embodiments, an output device 1106 may be in communication with the processor 1102. The output device 1106 may be disposed in the housing 701 of the respiratory training device 700. The output device 1106 may include the haptic device 768, a display device, an audio device, any other suitable output device, or any combination thereof. Examples of display devices include a screen, a touchscreen, or any other suitable display device, or any combination thereof. Examples of audio devices include a speaker, a bell, any other suitable audio device, or any combination thereof. In some embodiments, at least one input device 1108 may be in communication with the processor 1102. The input device 1108 may include the sensor 737, the sensor 775 of the connection element 712; any other suitable sensors, or any combination thereof. The input device 1108 may include a keyboard, a microphone, a touchscreen, any other suitable input device, or any combination thereof. In some embodiments, the processor 1102 may be connected to a network device 1110 configured for the processor 1102 to communicate with a a remote device, such as a mobile device (e.g. a mobile phone, a tablet, etc.), a laptop computer, a desktop computer, a server, or any other suitable device. The network device 1110 may be a wired or wireless device or adapter.

Figure 12:
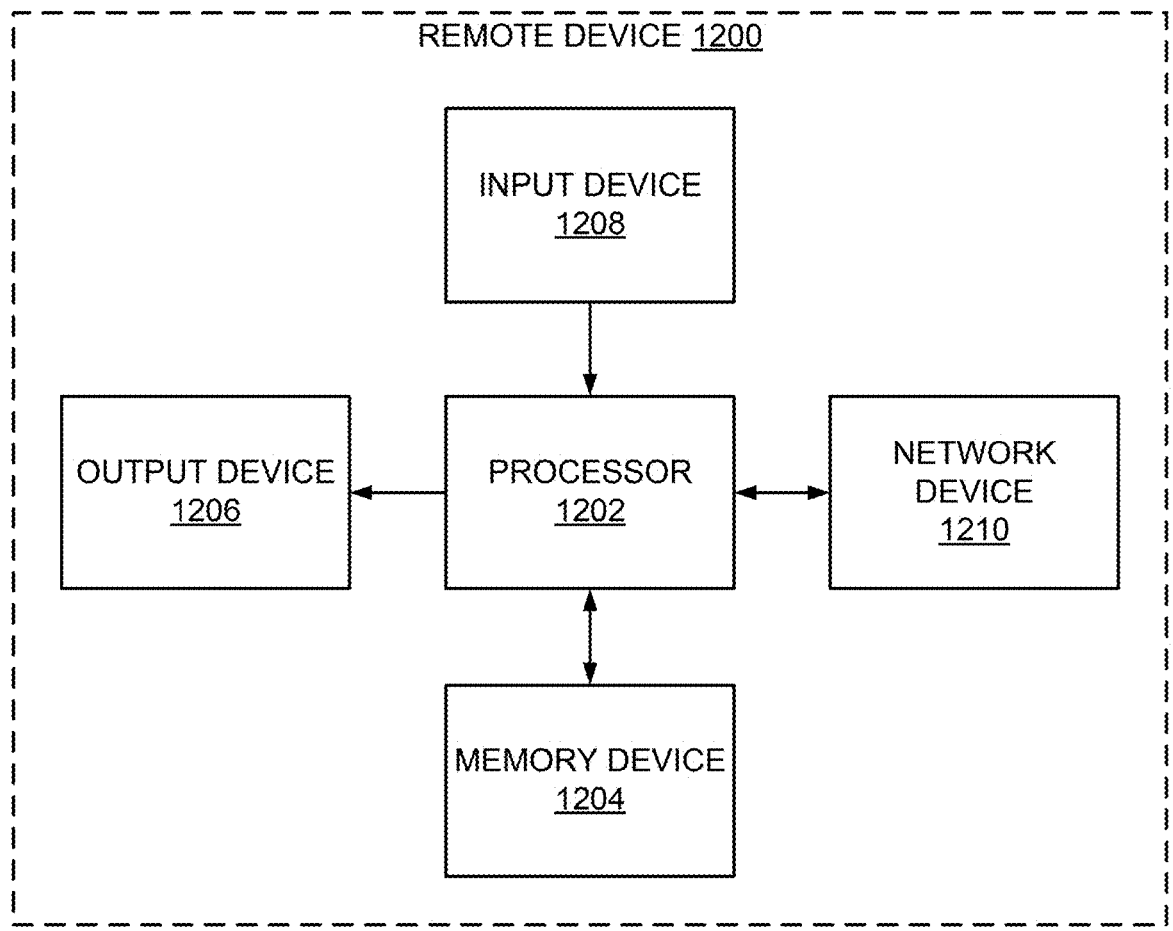
FIG. 12 is a block diagram of a mobile device in accordance with aspects of the present disclosure.

FIG. 12 illustrates a block diagram of a remote device 1200 for interfacing with the respiratory training device 700. The remote device 1200 may include a processor 1202 according to principles of the disclosure. The remote device 1200 may include a memory device 1204 in communication with the processor 1202. The memory device 1204 may be a hard-disc memory device, a solid state memory device, ROM, RAM, any other suitable memory device, or any combination thereof. The memory device 1204 may include instructions that cause the processor 1202 to perform certain operations, such as performing the methods disclosed herein.

In some embodiments, the remote device 1200 may include an output device 1206 in communication with the processor 1202. The output device 1206 may include a haptic device, a display device, an audio device, any other suitable output device, or any combination thereof. Examples of display devices include a screen, a touchscreen, or any other suitable display device, or any combination thereof. Examples of audio devices include a speaker, a bell, any other suitable audio device, or any combination thereof. The remote device 1200 may include at least one input device 1208 in communication with the processor 1202. The input device 1208 may include a sensor, a keyboard, a microphone, a touchscreen, any other suitable input device, or any combination thereof. The processor 1202 may be connected to a network device 1210 for allowing the processor 1202 to communicate with the respiratory training device 700. The network device 1210 may be a wired or wireless device or adapter.

Figure 13:
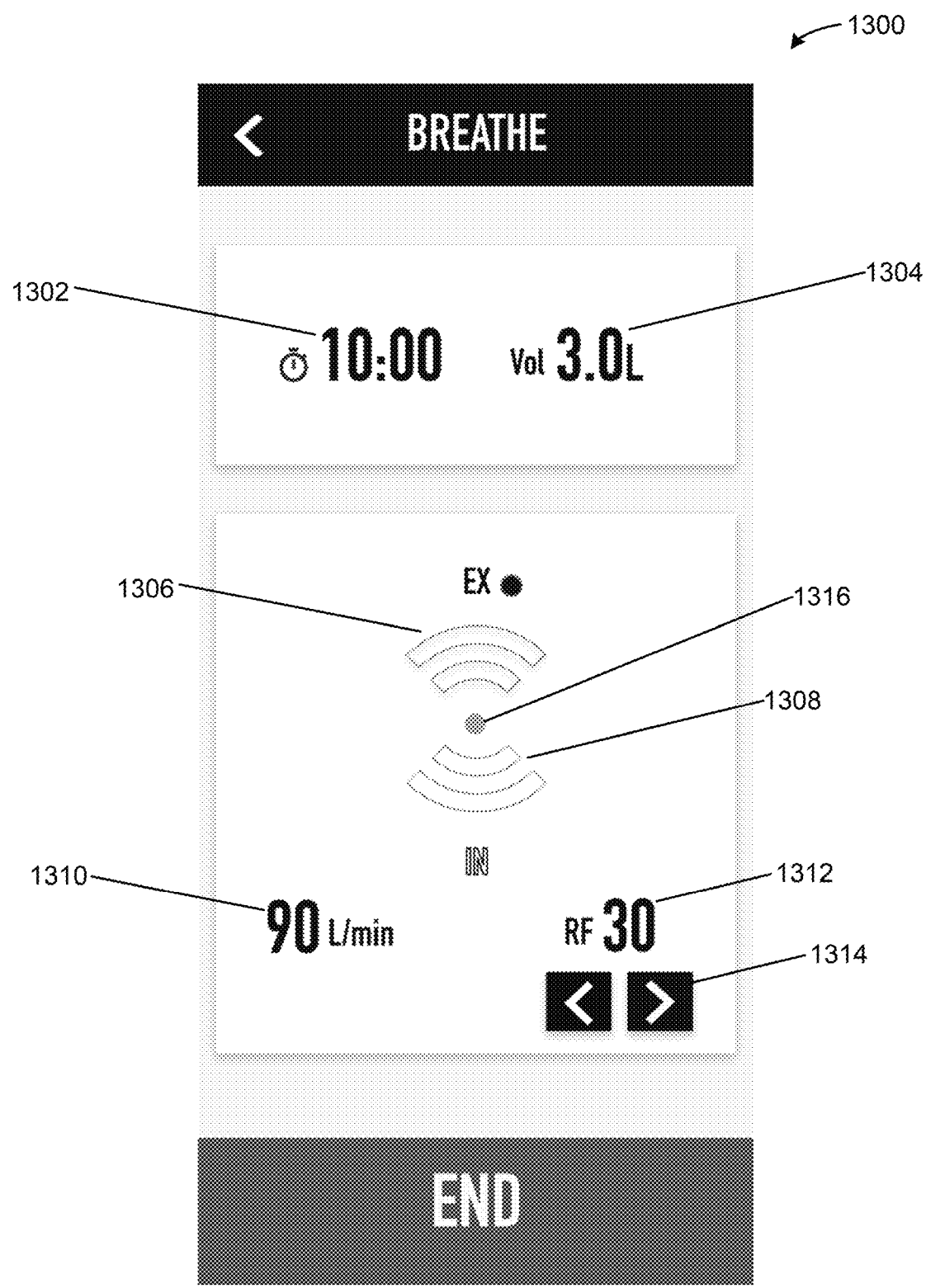
FIG. 13 is an illustration of an exemplary user interface for a computer application for use in connection with the respiratory training device.

FIG. 13 illustrates an example of a user interface 1300 for a mobile application for interfacing with a respiratory training device, such as respiratory training device 700. The user interface 1300 can include alternative arrangements including more or fewer design elements or features and positions of the elements or features. The mobile application and the user interface 1300 may be implemented on the remote device 1200. The user interface 1300 may include a timer graphical element 1302 to indicate a time left for an exercise. The timer graphical element 1302 may include a numerical time and/or a graphical element indicating that time remains for the session. The user interface 1300 may include an air bag volume graphical element 1304 to indicate the volume of the air bag 705. The air bag volume graphical element 1302 may include a numerical size (e.g., 3.0 L) and/or a graphical element indicating the size of the air bag 705. The user interface 1300 may include an exhalation graphical element 1306 to indicate that the user should exhale or to indicate that the user is exhaling. The user interface 1300 may include an inhalation graphical element 1308 to indicate that the user should inhale or to indicate that the user is inhaling. The user interface may include breathing volume rate indicator 1310 to indicate at what rate the user is or should be cycling air through his or her lungs (e.g., 90 L/min). The user interface 1300 may include a breathing frequency indicator graphical element 1312 to indicate how often (e.g. times per minute) the user is breathing or to indicate a breathing frequency target (e.g., RF 30). The user interface 1300 may include a breathing frequency target modifier graphical element 1314 to allow the user to modify the breathing frequency target. The user interface 1300 may include a readiness indicator 1316 for indicating that the user may start breathing into the respiratory training device 700. For example, the readiness indicator 1316 may display a green light to indicate that the respiratory training device 700 is ready for the user to begin the breath training exercise. The readiness indicator 1316 may display a red light to indicate that the respiratory training device 700 is not ready for the user to begin the breath training exercise.

The mobile application may include an option to select a mode. The option may include one or more modes for selection. The modes may include suitable breath training exercises, such as respiratory coordination training, respiratory technique training, slow twitch training, fast twitch training, and any other suitable breath training exercises. The mobile application may determine the tidal volume based on breathing information received from the sensor 737 and information about the size of the air bag 5. The mobile application may determine and display current respiratory frequency based on the breathing information. The mobile application may determine target respiratory frequency. The target respiratory frequency may be based on a user selection and/or modified based on the user selection. The target respiratory frequency may be based on a selected mode.

Figure 14:
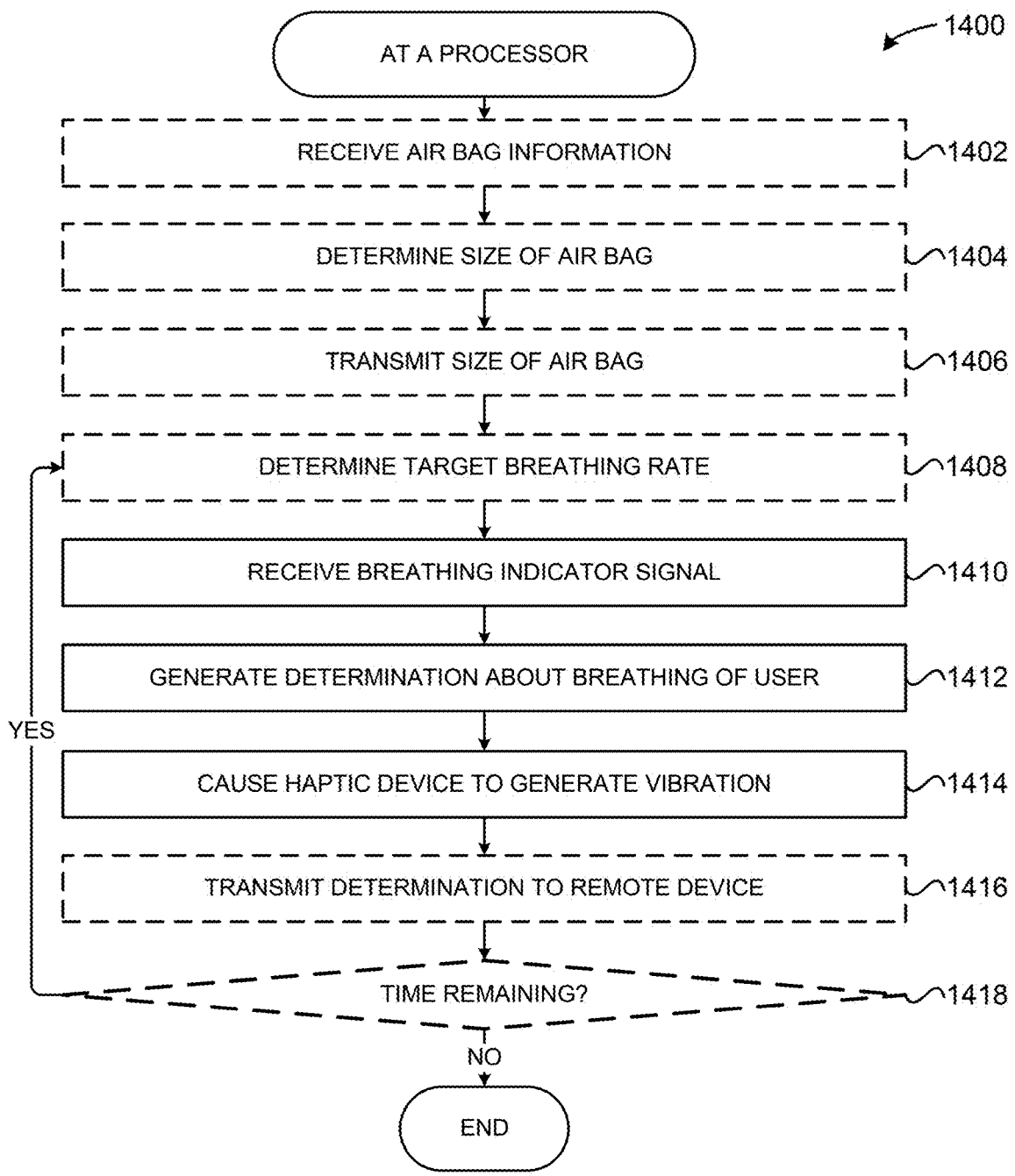
FIG. 14 is a process flow diagram of an exemplary method for the computer application of FIG. 13 for use in connection with the respiratory training device.

FIG. 14 illustrates a computer-implemented method 1400 for operating a respiratory training device. The respiratory training device may be the respiratory training device 700 or a respiratory device containing any suitable arrangement of its sub-components. The method 1400 may be implemented on a system including any suitable combination of elements of the respiratory training device 700. The method 1400 may be implemented on a system including the housing 701; the respiratory air channel 702; the processor 1102; the memory device 1104; the haptic device 768; and at least one breathing sensor, such as the sensor 737. The method 1400 may include operations that are implemented in computer instructions stored in a memory device, such as the memory device 1104, and executed by a processor, such as the processor 1102. The steps of the method 1400 may be stored in a non-transient computer-readable storage medium. The method 1400 may include more or fewer steps than those provided below, and those steps may be performed in any suitable order. The method 1400 may be implemented in a system to provide a user with breath training feedback.

At step 1402, the method 1400 may include receiving air bag information. For example, in some embodiments where the connection element 712 is in fluid communication with the respiratory air channel 702; the connection element 712 may be configured to receive an air bag 705; and where the connection element 712 is further configured to detect and transmit air bag information to the processor, for instance, by including a sensor, such as the sensor 775, for detecting air bag information; the processor 1102 may receive air bag information from the sensor 775 of the connection element 712. As another example, air bag information may be entered by the user through the input device 1108, the input device 1208, or any other suitable input device.

At step 1404, the method 1400 may include determining a size of the air bag 705. The size of the air bag 705 may be based on the air bag information. For example, in embodiments where the sensor 775 of the connection element 712 is a bar code reader and the processor 1102 has received the air bag information in the form of bar code information, the processor may determine the size of the air bag to be 3 L, 2.5 L, 2.0 L, 1.5 L or any other suitable size.

At step 1406, the method 1400 may include transmitting the size of the air bag to a remote device. For example, the processor 1102 may transmit information including that the air bag has a 3 L volume to a mobile device, such as the remote device 1200, a computer, or any other remote device, by way of the network device 1110.

At step 1408, the method 1400 may include determining a target breathing rate. The target breathing rate may be received from a remote device 1200. The target breathing rate may be entered at the input device 1208 of the remote device 1200. The target breathing rate may be entered through the input device 1108 of the respiratory training device 700. For example, the processor 1102 may receive the target breathing rate from a mobile device, such as the remote device 1200, by way of the network device 1110. The target breathing rate may change over time. For example, the user may change the target breathing rate using the input device 1108 of the respiratory training device 700 or the input device 1208 of the remote device 1200. The target breathing rate may be based on a respiratory training program.

At step 1410, the method 1400 may include receiving a breathing indicator signal from a sensor. For example, the processor 1102 can receive a signal from one or both of the sensor 767. In some embodiments, the sensor is (or sensors are) configured to detect whether air is being inhaled or exhaled. In some embodiments, a valve body 723 may be disposed in connection with the respiratory air channel 702. In some embodiments, the valve body 723 has a first position for receiving an inlet of fresh air and a second position for passing an outlet of exhaled air within the respiratory air channel. In some embodiments, the sensor is (or sensors are) configured to detect whether air is being inhaled from or exhaled into the respiratory training device 700. For example, the sensor detects whether the valve body 723 is in the first position (e.g., user is inhaling) or the second position (user is exhaling). For example, in embodiments where the sensors 737 are Hall sensors, the sensors 767 may detect whether the valve body 723 is in the first position or the second position by detecting the direction in which the valve body 723 is traveling.

At step 1412, the method 1400 may include generating a determination about the breathing of a user. The breath determination may be based on the breathing indicator signal. The breath determination about the breathing of the user may be based on a target breathing rate. The breath determination about the breathing of the user may be an overbreathing determination that the user is breathing too fast or an underbreathing determination that the user is breathing too slow. For example, the processor 1102 may determine that a user is breathing at a rate of 35 breaths per minute, when the target breathing rate is 30 breaths per minute, so the user is overbreathing. Alternatively, if the user is breathing too hard, as indicated by tidal volume, the processor may determine that the user is overbreathing. There may be an overbreathing threshold, such that, for example, given a target breathing rate of 30 breaths per minute, the user is only considered to be overbreathing once the user's target breathing rate exceeds 31.5 breaths per minute. There may be an underbreathing threshold, such that, for example, given a target breathing rate of 30 breaths per minute, the user is only considered to be underbreathing once the user's target breathing rate drops below 28.5 breaths per minute. For example, the processor 1202 can determine that a user is breathing at a rate of 35 breaths per minute, when the target breathing rate is 30 breaths per minute, so the user is overbreathing. Alternatively, if the user is breathing too hard, as indicated by tidal volume, the processor may determine that the user is overbreathing.

At step 1414, the method 1400 may include, responsive to the breath determination, causing the haptic device to generate a vibration. The haptic device may be configured to generate a first vibration pattern. The haptic device may be configured to generate a second vibration pattern. The second vibration pattern may be different from the first vibration pattern. The method 1400 may include causing the haptic device to generate the first vibration pattern in response to the overbreathing determination and the second vibration pattern in response to the underbreathing determination. For example, if the breath determination is that the user is overbreathing, the processor 1102 may cause the haptic device 768 to generate a series of long vibrational pulses. If the breath determination is that the user is underbreathing, the processor 1102 may cause the haptic device 768 to generate a series of short vibrational pulses. By generating different vibration patterns, the user can determine how to change his or her breathing to breath within the target breathing range.

At step 1416, the method 1400 may include transmitting the breath determination about the breathing of the user to a remote device. For example, the processor 1102 may transmit information including that the user is overbreathing, to a mobile device, such as the remote device 1200, by way of the network device 1110. The mobile device can be configured to display the information and/or provide an alert to the user.

At step 1418, the method 1400 may include determining whether there is remaining time. If there is remaining time in the exercise, the method 1400 may return back to another step. For example, the processor 1102 may determine that time remains based on the amount of time that has passed since a user started an exercise and return to step 1408 to determine if the target breathing rate is the same.

Figure 15:
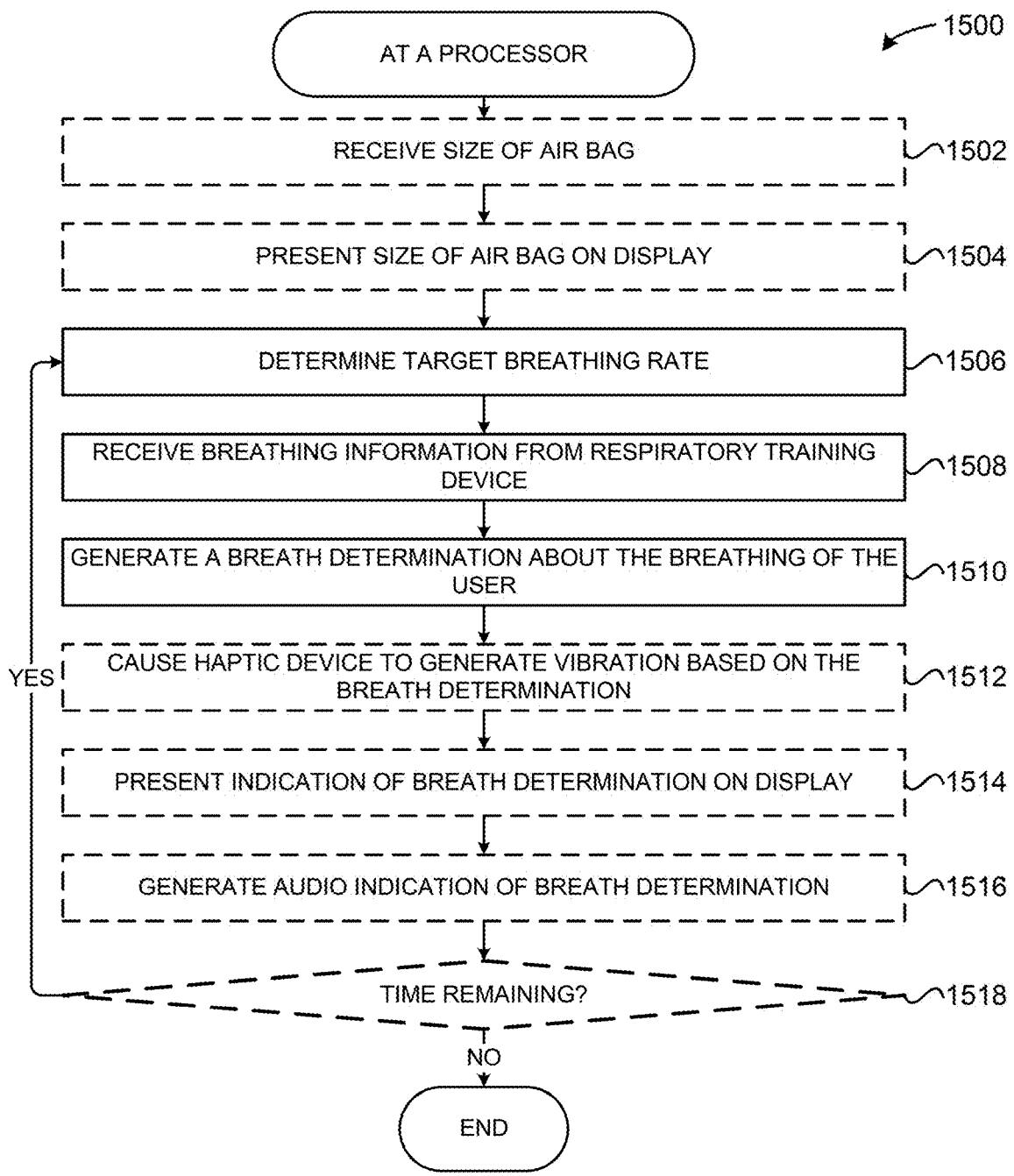
FIG. 15 is a process flow diagram of an exemplary method for using a respiratory training device of FIG. 7.

FIG. 15 illustrates a process flow diagram for a method 1500 of operating a mobile device in communication with a respiratory training device. The respiratory training device may be the respiratory training device 700 or a respiratory device containing any suitable arrangement of its subcomponents. The method 1500 may be implemented on a system including any suitable combination of elements of the remote device 1200. The method 1500 may be implemented on a system the processor 1202, the memory device 1204, the output device 1206, the input device 1208, and the network device 1210. The method 1500 may include operations that are implemented in computer instructions stored in a memory device, such as the memory device 1204, and executed by a processor, such as the processor 1202. The steps of the method 1500 may be stored in a non-transient computer-readable storage medium. The method 1500 may include more or fewer steps than those provided below, and those steps may be performed in any suitable order. The method 1500 may be implemented in a system to provide a user with breath training feedback.

At step 1502, the method 1500 may include receiving information including a size of an air bag from the respiratory training device. For example, the processor 1202 may receive information that the size of the air bag is 3 L, 2.5 L, 2.0 L, 1.5 L or any other suitable size by way of the network device 1110.

At step 1504, the method 1500 may include causing a display to present a graphical element indicating the size of the air bag. For example, the processor 1202 may cause a display embodiment of the output device 1206 of the remote device 1200 to present a graphical element indicating that the volume of the air bag is 3 L, as illustrated in FIG. 13.

At step 1506 the method 1500 may include determining a target breathing rate. The target breathing rate may be received from the respiratory training device 700. The target breathing rate may be entered at the input device 1208 of the remote device 1200. The target breathing rate may be entered through the input device 1108 of the respiratory training device 700. For example, the processor 1102 may receive the target breathing rate from a mobile device, such as the remote device 1200, by way of the network device 1110. The target breathing rate may change over time. For example, the user may change the target breathing rate using the input device 1108 of the respiratory training device 700 or the input device 1208 of the remote device 1200. The target breathing rate may be based on a respiratory training program.

At step 1508, the method 1500 may include receiving breathing information about a user's breathing from a respiratory training device. For example, the processor 1202 may receive information about a user's breathing rate from the respiratory training device 700 by way of the network device 1210. The breathing information may include information such as how many breaths per minute the user is experiencing, whether the user is overbreathing or underbreathing, or any other suitable breathing information. The breathing information may include the breathing indicator signal.

At step 1510, the method 1500 may include generating a breath determination of whether the user's breathing rate is above, below, or at the target breathing rate. There may be an overbreathing threshold, such that, for example, given a target breathing rate of 30 breaths per minute, the user is only considered to be overbreathing once the user's target breathing rate exceeds 31.5 breaths per minute. There may be an underbreathing threshold, such that, for example, given a target breathing rate of 30 breaths per minute, the user is only considered to be underbreathing once the user's target breathing rate drops below 28.5 breaths per minute. For example, the processor 1202 can determine that a user is breathing at a rate of 35 breaths per minute, when the target breathing rate is 30 breaths per minute, so the user is overbreathing. Alternatively, if the user is breathing too hard, as indicated by tidal volume, the processor may determine that the user is overbreathing.

At step 1512, the method 1500 may include causing a haptic device to vibrate based on the breath determination that the user's breathing rate is above or below the target breathing rate. The haptic device may be an output device 1206 of the remote device 1200 or the haptic device 768 of respiratory training device 700. The haptic device may be configured to generate a first vibration pattern. The haptic device may be configured to generate a second vibration pattern. The second vibration pattern may be different from the first vibration pattern. The method 1500 may include causing the haptic device to generate the first vibration pattern in response to the overbreathing determination and the second vibration pattern in response to the underbreathing determination. For example, if the breath determination is that the user is overbreathing, the processor 1102 may cause the haptic device 768 to generate a series of long vibrational pulses. If the breath determination is that the user is underbreathing, the processor 1102 may cause the haptic device 768 to generate a series of short vibrational pulses. By generating different vibration patterns, the user can determine how to change his or her breathing to breath within the target breathing range.

At step 1514, the method 1500 may include causing a display to present a graphical element indicating that the user's breathing rate is above or below the target breathing rate. For example, the processor 1202 may cause a display embodiment of the output device 1106 of the respiratory training device 700 (by way of the network device 1210) or a display embodiment of the output device 1206 of the remote device 1200 to present a graphical element indicating that the user's breathing rate is above or below the target breathing rate. As another example, red warning signals may appear on the user interface 1300 of the mobile application if the user is overbreathing, while blue underbreathing signals may appear on the user interface 1300 of the mobile application if the user is underbreathing.

At step 1516, the method 1500 may include causing the audio output device to generate a sound indicating that the user's breathing rate is above or below the target breathing rate. For example, if the user is overbreathing, the processor 1202 may cause a speaker embodiment of the output device 1206 to produce an alarm, while if the user is underbreathing, the processor 1202 may cause a speaker embodiment of the output device 1206 to produce a higher-pitched alarm.

At step 1518, the method 1500 may include determining whether there is remaining time. If there is remaining time in the exercise, the method 1500 may return back to another step. For example, the processor 1202 may determine that time remains and return to step 1506 to determine if the target breathing rate is the same.

In some embodiments, the respiratory training device may be configured to perform one or more of the functions discussed below.

Muscle recovery protocol training can be used to help a user's respiratory muscles recover as a form of therapy or to improve a user's exercise capacity and strength. For example, muscle recovery training may have a total duration of about twenty minutes. This exercise may simulate about 2000 meter to 2800 meter altitude via oxygen saturation of 90-94%. A user can begin the muscle recovery protocol training about one hour after the last meal of a user's day. The user can wear an oximeter, for example, on his or her finger. The air bag can have a volume of 1-1.5 liters. The user can breathe into the air bag lightly with little force as to not move the puck completely in the chamber. This will allow the user to drop the oxygen concentration in the arterial blood. The user can judge the level of desaturation by the oximeter and heart rate. If the user drops $O_2$ saturation too low, the user can take a big inhale bringing fresh air into the air bag and increasing their oxygen saturation. The goal is to keep oxygen saturation at 90-94% for twenty minutes. This will physiologically allow the user to increase blood flow and drop off more oxygen into the muscle increasing metabolism and increasing recovery.

Neuro relaxation protocol training may allow a user to relax more effectively. For example, an exercise for neuro relaxation protocol training may have a total duration of about 10 to 20 minutes. This exercise may increase $CO_2$ levels of the user resulting in oxygen saturation of about 90-95%. This exercise can be performed at any time of day. The user may wear an oximeter on the finger. The air bag can have a volume of 1-1.5 liters. The user may breathe into the bag lightly with little force as to not move the puck completely in the chamber. This may allow the user to drop the oxygen concentration in the arterial blood. The user may judge the level of desaturation by the oximeter and heart rate. If the user drops $O_2$ saturation too low, the user can take a big inhale bringing fresh air into the bag and increasing their oxygen saturation. The goal is to keep oxygen saturation at 90-94% for 20 minutes. This will physiologically allow the user to increase $CO_2$ levels in the blood and tissues, which may result in relaxing the user's nerves and muscles.

Increasing the vascularization of the lungs allows more blood to flow in and out of the lungs, enhancing the uptake of oxygen. For example, an exercise for increasing the vascularization of respiratory muscles may have a total duration of about twenty to forty minutes. This exercise may involve normocapnic breathing into the respiratory device at about 30-50% of max (Force Vital Capacity). The may breathe into a spirometer to attain force vital capacity in liters. The user may set the bag size to 30-50% of force vital capacity, start with a respiratory frequency of fifteen breaths per minute, and duration of 20-40 minutes. This may drive activation of the chest wall and stimulate building the capillary beds to the respiratory muscles.

Training of fast and slow-twitch respiratory muscle fibers may improve respiratory performance. For example, an exercise for respiratory muscle training of fast and slow-twitch fibers is disclosed. The user may have the ability to set the device as to elicit specific recruitment of the respiratory muscles. High force and velocity will activate fast-twitch fibers, while low force and velocity will activate slow-twitch fibers. For high force and velocity, the user can set the bag size to 60-100% of force vital capacity. For low force and velocity, user can set bag size to 30-50%.

Slow twitch training may have a duration of about twenty to forty minutes. Normocapnic breathing into the respiratory device may be at about 30-50% of maximum force vital capacity.

Fast-twitch training may have a duration of about thirty seconds to five minutes. Normocapnic breathing into the respiratory device may be at about 60-100% of maximum force vital capacity.

An exercise for vascular resistance manipulation may include inducing hypocapnia or hypercapnia for about 2-5 minutes pre-interval to manipulate vascular resistance, allowing vasoconstriction or vasodilation. The user may clip and enter a bag size of 1-1.5 liters. The user may then breathe for 2-5 minutes with the two warnings on the bottom of the coordination icon in the mobile application. This may create a slight state of hypoxia/hypercapnia. After the 2-5 minutes, the user may then breathe for 2-5 minutes based on the two warnings on the top of the coordination icon in the mobile application. This may create a slight state of hyperoxia/hypocapnia. The user is recommended to do this for only 10 minutes.

An exercise for mobilizing the costovertebral and intervertebral joints may include training on the respiratory device to mobilize the costovertebral and intervertebral joints via expansion and contraction of the rib cage during resisted breathing. During exercise or any postural activity, eccentric activity of the stabilizing muscles may occur except for diaphragm and pelvic floor which activate in a concentric manner. The diaphragm descends in a caudal direction, pressurizing intra-abdominal content from above, pelvic floor activates against; muscles of the chest and abdominal wall activate eccentrically like a belt, thus intra-abdominal pressure is increased, stabilizing the spine. In order for this to occur the initial alignment of the thorax is essential. If the thorax is not in alignment it creates issues for physiologically balanced breathing and postural stabilization of the trunk. The neutral position, in which breathing and stabilization should occur without excessive activation of accessory muscles (i.e. sternocleidomastoids, scalenes, pectoralis) is considered an alignment of the thorax in which the clavicles form a 25-30-degree angle from the horizontal while the thoracic spine is erect, though great individual variation occurs. The alignment of the rib cage should ideally correspond to the position of the pelvis. The goal is that when the thoracic spine is erect, the rib cage is positioned parallel to the pelvis and the centrum tendineum of the diaphragm is on a horizontal plane. Such alignment of the thorax allows for the centrum tendineum to act in a caudal direction, as a piston against the pelvic floor. From a developmental perspective, this harmony and the above-described alignment of the pelvis and the thorax to one another should already be ensured at the age of 4½ months. This is the time when stabilization of the thorax, spine and pelvis in the sagittal plane is completed as a basic prerequisite to locomotor function of the extremities. In later stages, when the child attains quadruped, sitting and standing positions, the child uses the ideal breathing pattern described above, activates the same stabilizing muscle co-activation during exertion and the same mutual alignment between the pelvis and the thorax while the spine is erect.

Initial respiratory postural movements begin the first active positions a newborn baby initiates around 3-5 months. Then moving sequentially into more dynamic movements and postures. By using the respiratory training device's dual resistance during the inhale and exhale improved musculoskeletal function can be re-acquired by returning to developmental stages of movement and re-grooving balanced movement in the presence of proper diaphragmatic breathing and stabilization. Some respiratory exercises based on respiratory postural movement development are discussed below. For several of these exercises, it is important for the user to be able to grip the handle of the respiratory device with both hands in order to assist the user in maintaining the correct posture.

A first example exercise position is based on the prone developmental stage (3 months of age) with elbows on the ground. This prone position is particularly effective for thoracic extension stretching and shoulder stability. Along with still having control over breathing patterns, and abdominal stability. The user holds the training device with their hands in the prone position and breathes into the device.

A second example exercise position is based on a (3 months of age) supine position with knees elevated. This position may help eliminate lower back pain, improves diaphragmatic breathing, and decreases stress on the spine. It initiates the basics of trunk stability to create a stable spine to be the foundation for movement through the upper and lower extremities. The individual holds the respiratory training device with their hands in the 90-90 supine position and breathes into the device.

A third example exercise position is based on the quadruped position on hands and knees (7 months of age). This position challenges rotary stability and develops reciprocal motion allowing for unloaded spinal stability. The individual may hold the respiratory training in one hand while stabilizing the body with the other three points of stability. During the inhale phase of the movement, the individual may go through increased spinal flexion and posterior pelvic tilt. During the exhale movement the individual may go through neck and spinal extension along with anterior pelvic tilt.

A fourth example exercise position is based on the base stance standing posture with the feet spread shoulder-width apart. The respiratory training is held in the hands. During the inhale phase of the movement, the pelvis is driven into a posterior pelvic tilt and elbows are raised apart. This allows for optimal pelvic floor activation and external rotation of the rib cage. Along with eccentric lengthening of the abdominal muscles creating a 360-degree expansion of the rib cage. During the exhale phase of movement the pelvis is driven into anterior pelvic tilt and elbows are pulled down together. This allows for the rib cage to internally rotate creating concentric activation of the abdominals.

A fifth example exercise position is based on the identical base stance as the fourth example exercise position. During the first inhale phase of the movement, the pelvis is driven into a posterior pelvic tilt during that movement bilateral elbows are lifted and rotated to the right as far as possible. During the exhale phase the pelvis is driven into an anterior pelvic tilt as the elbows are rotated from the right rotated position back to neutral position together in front of the body. During the second inhale phase the pelvis is driven back into a posterior pelvic tilt and elbows are elevated and left rotated as far as possible. This rotation allows for eccentric lengthening of the rotational facial sling from opposite hip to the opposite shoulder. It also allows for the opposite (left posterior lumbar/right anterior chest wall) intra-abdominal and thoracic pressures to be increased during inhalation.

A sixth example exercise position is based on the left foot facing forward and the right foot dropped into an R 45 degree posterior lunge. During the inhalation phase of the movement the body's center of mass is shifted over the right foot and hip with right trunk rotation. During the exhale phase of the movement the left knee is driven into flexion and the trunk left rotates bringing the center of mass over the left ankle. Both these positions create bilateral hip internal rotation from the top down and bottom-up, both are important positions for optimal locomotor function.

An exercise for strength training of accessory breathing muscles (cervical, thoracic, abdominals) may include resisted exhales with the respiratory training device to stimulate and strength accessory muscles (30 muscles used in the respiration cycle.) These accessory muscles are the cervical, thoracic, and abdominal muscles. Strength training may be considered to be anytime the user uses a bag size of 75% or greater of their forced vital capacity. The user can do 3 sets of 5 minutes at a respiratory frequency of 0-30 breaths per min, using a 5 min rest between sets. This may train and strengthen accessory and respiratory muscles.

Inspiration/expiration training may include variable resistance inhalations and exhalations of the respiratory cycle. Three exemplary methods for inspiration/expiration training may include (i) increasing the inhalation force followed by a slow exhalation may create an eccentric lengthening of the intercostal muscles with the dissipation of eccentric elasticity during the concentric oriented exhalation; (ii) increasing the exhalation force followed by a slow exhalation will create a concentric dominated exhalation within the intercostal muscles, with a slow twitch dominated eccentric lengthening during the inhalation; and (iii) increased inhalation force followed by a pause then increased exhalation force followed by a pause and repeat; this is sport specific to swimming, and may create an eccentric lengthening of the intercostal muscles with the dissipation of eccentric elasticity during the concentric oriented exhalation.

An exercise for respiratory technique training may include increasing the efficiency of the breathing mechanics of the respiratory cycle. Users can set bag size to 30-50% FVC and respiratory frequency of 0, duration of 1-5 minutes. Users may do as many sets as able until technical failure. Keys targets for the user are having diaphragmatic and sternal breathing syncing and rising and falling together, while managing intra-abdominal pressure via internal obliques and elongation of the lumbar erectors during inhale and exhale.

An exercise for gas exchange manipulation may include manipulating $CO_2$ and $O_2$ exchange during the breathing cycle. Increasing $CO_2$ and decreasing $O_2$ creating a vasodilation and vice versa increasing $O_2$ and decreasing $CO_2$ may create a vasoconstriction. Both gas exchange manipulations can be used for training the cardiac system and the bioenergetic system.

Respiratory frequency evaluation may include a respiratory counter that tracks the number of exhalations, inhalations, or both.

Respiratory coordination training may include training to coordinate breathing at high frequencies. Sync inhale and exhale to the exact same volume of air moved in and out of the lungs. To accomplish this the user may use a bag size equal to 20-30% of forced vital capacity. Setting the respiratory frequency 20-80 breaths per minute. Interval length is 30 seconds to 2 minutes with a 1:2 work to rest ratio. Users can perform 6-30 sets. The use of visual feedback (blinking LED, display, etc.), audio feedback, or haptic feedback may assist with this.

Figure 16:
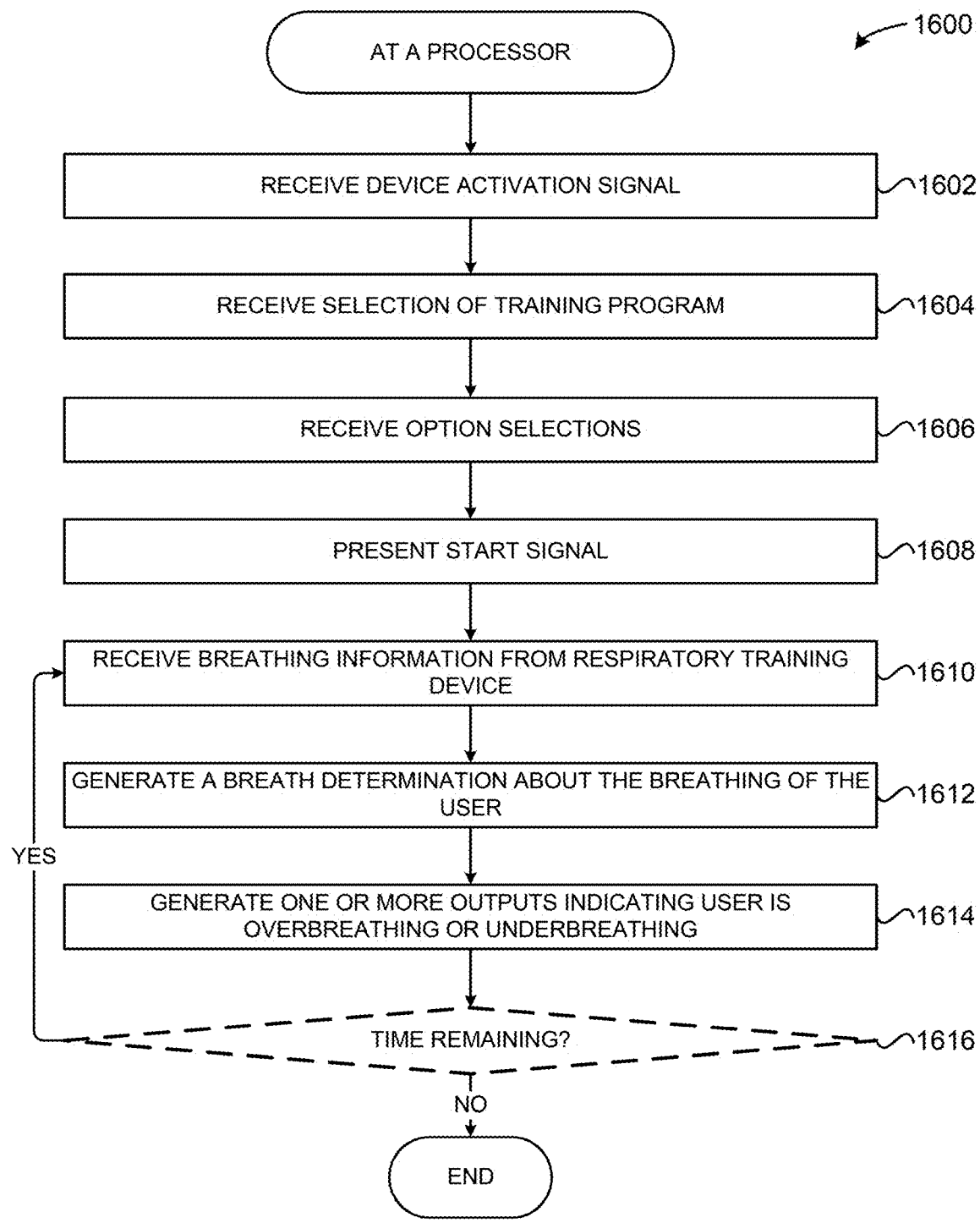
FIG. 16 is a process flow diagram of an exemplary method for using the respiratory training device of FIG. 7.

FIG. 16 illustrates a process flow diagram for a method 1600 for respiratory coordination training on a respiratory training device, such as the respiratory training device 700, in communication with a mobile device, such as the remote device 1200, including a mobile application. The respiratory training device may be the respiratory training device 700 or a respiratory device containing any suitable arrangement of its sub-components. The method 1600 may be implemented on a system including any suitable combination of elements of the remote device 1200. The method 1600 may be implemented on a system the processor 1202, the memory device 1204, the output device 1206, the input device 1208, and the network device 1210. The method 1600 may include operations that are implemented in computer instructions stored in a memory device, such as the memory device 1204, and executed by a processor, such as the processor 1202. The steps of the method 1600 may be stored in a non-transient computer-readable storage medium. The method 1600 may include more or fewer steps than those provided below, and those steps may be performed in any suitable order. The method 1600 may be implemented in a system to provide a user with breath training feedback.

At step 1602, the method 1600 may include receiving a device activation signal. For example, the user may press an "ON" button on the respiratory training device 700.

At step 1604, the method 1600 may include receiving a selection of the respiratory coordination training program. For example, the mobile application of the remote device 1200 may present, on the display of the remote device 1200, a selection of different training programs, and the user may select the respiratory coordination training program.

At step 1606, the method 1600 may include receiving one or more option selections. For example, the mobile application of the remote device 1200 may present, on the display of the remote device 1200, several fields which may include time, respiratory frequency, and bag size; and the user may enter values or make selections of time, respiratory frequency, and bag size. If the user chooses zero as the respiratory frequency, the user may breathe at their own pace.

At step 1608, the method 1600 may include presenting a start signal. For example, the display of the remote device 1200 may present the user interface 1300, which may present a green light as a readiness indicator 1316.

At step 1610, the method 1600 may include receiving breathing information about a user's breathing from a respiratory training device. For example, the processor 1202 may receive information about a user's breathing rate from the respiratory training device 700 by way of the network device 1210. The breathing information may include information such as how many breaths per minute the user is experiencing, whether the user is overbreathing or underbreathing, or any other suitable breathing information. The breathing information may be a breathing indicator signal.

At step 1612, the method 1600 may include generating a breath determination of whether the user's breathing rate is above, below, or at the target breathing rate. There may be an overbreathing threshold, such that, for example, given a target breathing rate of 30 breaths per minute, the user is only considered to be overbreathing once the user's target breathing rate exceeds 31.5 breaths per minute. There may be an underbreathing threshold, such that, for example, given a target breathing rate of 30 breaths per minute, the user is only considered to be underbreathing once the user's target breathing rate drops below 28.5 breaths per minute. For example, the processor 1202 can determine that a user is breathing at a rate of 35 breaths per minute, when the target breathing rate is 30 breaths per minute, so the user is overbreathing. Alternatively, if the user is breathing too hard, as indicated by tidal volume, the processor may determine that the user is overbreathing. As another example, the processor 1202 can determine that, based on the breathing information indicating that the user is overbreathing, the user is overbreathing.

At step 1614, the method 1600 may include generating one or more outputs indicating that the user is overbreathing or underbreathing. For example, if the breath determination is that the user is overbreathing, the mobile application may present at the top of the user interface 1300 one warning bar with the words "slow down" over the warning bar; if the user continues overbreathing, the mobile application may present at the top of the user interface two warning bars, the haptic device 768 of the respiratory training device 700 will vibrate with long vibrational pulses; and if the user further continues overbreathing, the respiratory training device 700 will be shut down. An another example, if the breath determination is that the user is underbreathing, the mobile application may present at the top of the user interface 1300 one warning bar with the words "speed up" over the warning bar; if the user continues underbreathing, the mobile application may present at the top of the user interface two warning bars, the haptic device 768 of the respiratory training device 700 will vibrate with short vibrational pulses; and if the user further continues underbreathing, the respiratory training device 700 will be shut down. The time between the escalating indications (one warning bar, two warning bars and vibrational pulses, and shutdown) may be selected by the user or determined based on a calculation relative to the bag size. Note that the processes discussed in step 1614 may be applied to the other methods of this disclosure.

At step 1616, the method 1600 may include determining whether there is remaining time. If there is remaining time in the exercise, the method 1600 may return back to another step. For example, the processor 1102 may determine that time remains and return to step 1610 to receive updated breathing information.

An exercise for respiratory endurance training may include increasing the resistance to fatigue for the respiratory muscles and increasing the functional capacity to move air during high intensity or volume activities. The user may breathe in a spirometer to attain forced vital capacity in liters. The user may set the bag size to 30-50% of forced vital capacity, starting respiratory frequency of 15 breaths per minute, and duration of 20-40 minutes. This will drive activation of the chest wall and stimulate building the capillary beds to the respiratory muscles.

An exercise for left cardiac ventricle training may include creating a hypocapnic environment such that vasoconstriction will increase preload to stimulate stroke volume, improving left ventricular hypertrophy. Due to a hypertrophy of the right side of the heart (overloaded) the user may train the left side of the heart and relax the right side. The goal is that the blood vessels are vasoconstricted where the blood of the pulmonary system will open and the blood vessels of systemic circulatory system constrict, so the left ventricular has to pump more-training on the respiratory training device to be hypocapnic by over breathing. Further, the user can perform interval training by creating a venous occlusion and hold as long as possible and release until total hemoglobin is recovered (total hemoglobin is the guide). Another method is to increase stroke volume by changing position (i.e. recumbent bike and tilt to 45 degrees where your legs are up and the blood goes back also lifting weights on a 45 degree angle). Better yet, is both total hemoglobin & positional. The user is suggested to first increase cardiac output for 30 sec. then engage in venous occlusion (i.e. bike then in an athletic stance with a load that creates the occlusion by holding isometrically then jump to a 45 degree exercise and continue to move keeping the total hemoglobin increasing). When released, there may be a preload on the right side of the heart and then a transfer to the left side. The user may then, in hockey stance, hyperventilate into the respiratory training device to overbreathe. The user may use indicators on the user interface 1300 of the mobile device 1200 or on the respiratory to determine that the user is overbreathing.

An exercise for right cardiac ventricle training may include creating a hypercapnic environment that may increase the peripheral vascular dilation but will move blood away from the right ventricle, making it work harder. This may strengthen the right ventricle of the heart. Training the right side of heart may require a vasoconstriction in the lungs and vasodilation in the systemic system by creating a lot of $CO_2$ (i.e. interval training on a bike or treadmill with respiratory training device, using slow, controlled motion) with a critical peripheral capillary oxygen saturation ($SpO_2$), the percentage of oxygenated haemoglobin (haemoglobin containing oxygen) compared to the total amount of haemoglobin in the blood (oxygenated and non-oxygenated haemoglobin), of 90-92%.

Altitude simulation may include using the respiratory training device to stimulate altitude physiological environments. As a user goes hypercapnic the user may shift the $O_2$ dissociation curve to the right (easy access to $O_2$ but hard to load), and $SpO_2$ may be sustained in the range 90-92%. This is a hypoxic/hypercapnic state which may create an EPO stimulation (increases red blood cell production) and an increase the hormone DPG (because of the increase in intensity training) which assists in desaturation (unloading) therefore increases utilization along with intercoordination (using more muscles).

An exercise for hyperoxia training may include inducing a hypocapnic environment to increase $O_2$ percent saturation. This can be used to recover from intensive exercise. If high $CO_2$ after intensive exercise or mental state, then hyperoxia breath training to balance $CO_2/O_2$ may create homeostasis and lessen recovery time and energy expenditure.

Hypoxia training may include inducing a hypercapnic environment to decrease $O_2$ percent saturation. This can be used to deliver more blood to the peripheral muscles. To decrease recovery time from training, hypoxic breath training will increase $CO_2$ causing a vasodilation and decreasing inflammation.

Respiratory disease therapy for chronic obstructive pulmonary disease & pulmonary fibrosis may improve the efficiency of the respiratory muscles. Maintaining the slow twitch muscle architecture (mitochondria and vascularization) may allow the respiratory muscles to resist fatigue and degeneration.

In some embodiments, one or more of the following components or equipment can be integrated or incorporated in to the respiratory training device.

In some embodiments, the respiratory training device includes a peak flow meter that measures the maximum speed of expiration. The peak flow meter measures the airflow through the bronchi and thus the degree of obstruction in the airways. Peak expiratory flow (PEF) is typically measured in units of liters per minute (L/min). The peak flow meter works by measuring how fast air comes out of the lungs when you exhale forcefully after inhaling fully.

In some embodiments, the respiratory training device includes a spirometer that measures the volume of air inspired and expired by the lungs. A spirometer measures ventilation, the movement of air into and out of the lungs. The spirogram will identify two different types of abnormal ventilation patterns: obstructive and restrictive.

In some embodiments, the respiratory training device includes a $SpO_2$ sensor for pulse oximetry to monitor a person's peripheral oxygen saturation. The device passes two wavelengths of light through the body part to a photodetector. It measures the changing absorbance at each of the wavelengths, allowing it to determine the absorbances due to the pulsing arterial blood alone, excluding venous blood, skin, bone, muscle, fat, etc.

In some embodiments, the respiratory training device includes a capnometer for monitoring $ETCO_2$ (end tidal $CO_2$, the partial pressure or maximal concentration of $CO_2$ at the end of an exhaled breath) a monitoring device that measures and numerically displays the concentration of carbon dioxide in exhaled air. In some embodiments, the respiratory training device may be configured for evaluating end tidal $CO_2$—$CO_2$ concentration of end volume of the air that is exhaled in the respiration cycle.

In some embodiments, the respiratory training device includes a respiratory frequency monitor.

In some embodiments, the respiratory training device includes a temperature sensor.

In some embodiments, the respiratory training device includes a pressure sensor. Low pressure sensors may be based on thermal flow measurement of gas through a microflow channel integrated within the sensor chip.

In some embodiments, the respiratory training device includes a gas exchange analyzer. The gas exchange analyzer may analyze expired percentages of $O_2$ and $CO_2$. The exchange of gases ($O_2$ & $CO_2$) between the alveoli and blood occurs by simple diffusion: $O_2$ diffusing from the alveoli into the blood and $CO_2$ from the blood into the alveoli.

In some embodiments, the respiratory training device includes an oxygen sensor that further measures humidity percent humidity. The sensor detects the variation in relative humidity that occurs between inhaled and exhaled breath. A sensor interrogation system may determine the breathing pattern in real time and can also predict the breathing rate and the breathing status during respiration.

In some embodiments, the respiratory training device may be configured for evaluating $VO_2$ max, also known as maximal oxygen uptake. $VO_2$ max is the measurement of the maximum amount of oxygen a person can utilize during intense exercise. It is a common measurement used to establish the aerobic endurance of an athlete prior to or during the course of training.

In some embodiments, the respiratory training device may be configured for oximetry evaluation, evaluating arterial saturation of $O_2$ percent.

Consistent with the above disclosure, the examples of systems and method enumerated in the following clauses are specifically contemplated and are intended as a non-limiting set of examples.

Clause 1 A system for respiratory training, comprising:
a housing;
a respiratory air channel disposed within the housing;
a sensor configured to detect a breathing indicator and transmit a breathing indicator signal;
a haptic device disposed within the housing;
a processor operatively coupled to the sensor and the haptic device; and
a memory device operatively coupled to the processor, the memory device comprising instructions that, when executed by the processor, cause the processor to:
receive the breathing indicator signal from the sensor;
generate a breath determination based on the breathing indicator signal; and
responsive to the breath determination, cause the haptic device to generate a vibration.

Clause 2. The system of any preceding clause, further comprising:
a valve body disposed in connection with the respiratory air channel, the valve body having a first position and a second position within the respiratory air channel
wherein the sensor is configured to detect if the valve body is in a first position or a second position.

Clause 3. The system of any preceding clause, wherein the breath determination is selected from a group comprising a target breathing determination that the user is within a target range, an overbreathing determination that the user is breathing too fast, or an underbreathing determination that the user is breathing too slow.

Clause 4. The system of any preceding clause, wherein, responsive to the overbreathing determination, the haptic device is configured to generate a first vibration pattern, and responsive to the underbreathing determination, the haptic device is configured to generate a second vibration pattern.

Clause 5. The system of any preceding clause, wherein the second vibration pattern is different from the first vibration pattern.

Clause 6. The system of any preceding clause, further comprising:
a connection element in fluid communication with the respiratory air channel, wherein the connection element is configured to couple to an air bag; and
wherein the connection element comprises a sensor that is configured to detect and transmit air bag information to the processor.

Clause 7. The system of any preceding clause, further comprising:
a network device operatively coupled to the processor; and
wherein the instructions further cause the processor to:
receive the air bag information;
determine a size of the air bag based on the air bag information; and
transmit the size of the air bag to a remote device.

Clause 8. The system of any preceding clause, further comprising:
a network device operatively coupled to the processor; and
wherein the instructions further cause the processor to transmit the breath determination about the breathing of the user to a remote device.

Clause 9. The system of any preceding clause, wherein the housing comprises a handle defines a handle opening having a width of at least 1.5 inches.

Clause 10. The system of any preceding clause, further comprising:
the housing including a handle;
the housing including a compartment disposed opposite the handle; and
a battery disposed within the compartment.

Clause 11. The system of any preceding clause, further comprising:
a remote device, the remote device comprising:
a remote display;
a remote network device;
a remote processor operatively coupled to the display and the network device; and
a remote memory device operatively coupled to the remote processor, the memory device comprising remote instructions that, when executed by the remote processor, cause the remote processor to:
determine a target breathing rate;
receive breathing information about a user's breathing from the processor; and
generate a remote breath determination of whether the user's breathing rate is above or below the target breathing rate.

Clause 12. A system for respiratory training, comprising:
a housing;
a respiratory air channel disposed within the housing;
a sensor configured to detect a breathing indicator and transmit a breathing indicator signal; and
a haptic device disposed within the housing and configured to provide haptic feedback in response to the breathing indicator signal.

Clause 13. The system of any preceding clause, further comprising:
a valve disposed in connection with the respiratory air channel, the valve having a first position and a second position; and
wherein the sensor is configured to detect whether air is being inhaled or exhaled by detecting whether the valve is in the first position or the second position.

Clause 14. The system of any preceding clause, wherein the haptic device is configured to generate a first vibration pattern and a second vibration pattern that is different from the first vibration pattern.

Clause 15. The system of any preceding clause, further comprising:
the housing including a handle;
the housing including a compartment disposed opposite the handle; and
a battery disposed within the housing compartment.

Clause 16. A system for providing a user with breath training feedback, comprising:
a display;
a network device;
a processor operatively coupled to the display and the network device; and
a memory device operatively coupled to the processor, the memory device comprising instructions that, when executed by the processor, cause the processor to:
determine a target breathing rate;
receive breathing information about a user's breathing from a respiratory training device; and
generate a breath determination of whether the user's breathing rate is above or below the target breathing rate.

Clause 17. The system of any preceding clause, wherein the instructions further cause the processor to:
cause a haptic device to vibrate based on the breath determination that the user's breathing rate is above or below the target breathing rate.

Clause 18. The system of any preceding clause, wherein the instructions further cause the processor to cause the display to present a graphical element indicating that the user's breathing rate is above or below the target breathing rate.

Clause 19. The system of any preceding clause, further comprising:
an audio output device in communication with the processor; and
wherein the instructions further cause the processor to cause the audio output device to generate a sound indicating that the user's breathing rate is above or below the target breathing rate.

Clause 20. The system of any preceding clause, wherein the instructions further cause the processor to:
receive information comprising a size of an air bag from the respiratory training device; and
cause the display to present the size of the air bag.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A system for respiratory training, comprising:
a housing;
a respiratory air channel disposed within the housing;
a sensor configured to detect a breathing indicator and transmit a breathing indicator signal;
a haptic device disposed within the housing;
a processor operatively coupled to the sensor and the haptic device; and
a memory device operatively coupled to the processor, the memory device comprising instructions that, when executed by the processor, cause the processor to:
receive the breathing indicator signal from the sensor;
generate a breath determination based on the breathing indicator signal;
responsive to the breath determination, cause the haptic device to generate a vibrations;
a connection element in fluid communication with the respiratory air channel, wherein the connection element is configured to couple to an air bag; and
wherein the connection element comprises a sensor that is configured to detect and transmit air bag information to the processor.

2. The system of claim 1, further comprising:
a valve body disposed in connection with the respiratory air channel, the valve body having a first position and a second position within the respiratory air channel
wherein the sensor is configured to detect if the valve body is in a first position or a second position.

3. The system of claim 1, wherein the breath determination is selected from a group comprising a target breathing determination that a user is within a target range, an overbreathing determination that the user is breathing too fast, or an underbreathing determination that the user is breathing too slow.

4. The system of claim 3, wherein, responsive to the overbreathing determination, the haptic device is configured to generate a first vibration pattern, and responsive to the underbreathing determination, the haptic device is configured to generate a second vibration pattern.

5. The system of claim 4, wherein the second vibration pattern is different from the first vibration pattern.

6. The system of claim 1, further comprising:
a network device operatively coupled to the processor; and
wherein the instructions further cause the processor to:
receive the air bag information;
determine a size of the air bag based on the air bag information; and
transmit the size of the air bag to a remote device.

7. The system of claim 1, further comprising:
a network device operatively coupled to the processor; and
wherein the instructions further cause the processor to transmit the breath determination about the breathing of the user to a remote device.

8. The system of claim 1, wherein the housing comprises a handle defines a handle opening having a width of at least 1.5 inches.

9. The system of claim 1, further comprising:
the housing including a handle;
the housing including a compartment disposed opposite the handle; and
a battery disposed within the compartment.

10. The system of claim 1, further comprising:
a remote device, the remote device comprising:
a remote display;
a remote network device;
a remote processor operatively coupled to the remote display and the remote network device; and
a remote memory device operatively coupled to the remote processor, the memory device comprising remote instructions that, when executed by the remote processor, cause the remote processor to:
determine a target breathing rate;
receive breathing information about a user's breathing from the processor; and
generate a remote breath determination of whether the user's breathing rate is above or below the target breathing rate.

11. A system for respiratory training, comprising:
a housing;
a respiratory air channel disposed within the housing;
a sensor configured to detect a breathing indicator and transmit a breathing indicator signal;
a haptic device disposed within the housing and configured to provide haptic feedback in response to the breathing indicator signal;
the housing including a handle;
the housing including a compartment disposed opposite the handle; and
a battery disposed within the housing compartment.

12. The system of claim 11, further comprising:
a valve disposed in connection with the respiratory air channel, the valve having a first position and a second position; and
wherein the sensor is configured to detect whether air is being inhaled or exhaled by detecting whether the valve is in the first position or the second position.

13. The system of claim 11, wherein the haptic device is configured to generate a first vibration pattern and a second vibration pattern that is different from the first vibration pattern.

14. A system for providing a user with breath training feedback, comprising:
a display;
a network device;
a processor operatively coupled to the display and the network device; and
a memory device operatively coupled to the processor, the memory device comprising instructions that, when executed by the processor, cause the processor to:
determine a target breathing rate;
receive breathing information about a user's breathing from a respiratory training device;
generate a breath determination of whether the user's breathing rate is above or below the target breathing rate;
receive information comprising a size of an air bag from the respiratory training device; and
cause the display to present the size of the air bag.

15. The system of claim 14, wherein the instructions further cause the processor to:
cause a haptic device to vibrate based on the breath determination that the user's breathing rate is above or below the target breathing rate.

16. The system of claim 14, wherein the instructions further cause the processor to cause the display to present a graphical element indicating that the user's breathing rate is above or below the target breathing rate.

17. The system of claim 14, further comprising:
an audio output device in communication with the processor; and wherein the instructions further cause the processor to cause the audio output device to generate a sound indicating that the user's breathing rate is above or below the target breathing rate.

* * * * *